(12) United States Patent
Stack et al.

(10) Patent No.: US 11,000,637 B2
(45) Date of Patent: May 11, 2021

(54) SYSTEMS AND METHODS FOR TRANSSEPTAL DELIVERY OF PERCUTANEOUS VENTRICULAR ASSIST DEVICES AND OTHER NON-GUIDEWIRE BASED TRANSVASCULAR THERAPEUTIC DEVICES

(71) Applicant: Synecor LLC, Chapel Hill, NC (US)

(72) Inventors: Richard S Stack, Chapel Hill, NC (US); William L Athas, Chapel Hill, NC (US); Kevin Johnson, Durham, NC (US); Emer M Feerick, Galway (IE); Matthew Moran, Galway (IE); Damian Muldoon, Galway (IE); Liam Ruddy, Mayo (IE); William Cannon, Galway (IE); Rory O'Brien, Tipperary (IE)

(73) Assignee: SYNECOR LLC, Durham, NC (US)

( * ) Notice: Subject to any disclaimer, the term of this patent is extended or adjusted under 35 U.S.C. 154(b) by 0 days.

(21) Appl. No.: 16/578,373

(22) Filed: Sep. 22, 2019

(65) Prior Publication Data

US 2020/0254163 A1    Aug. 13, 2020

Related U.S. Application Data

(60) Provisional application No. 62/802,212, filed on Feb. 7, 2019.

(51) Int. Cl.
*A61M 1/12*     (2006.01)
*A61M 25/09*    (2006.01)
(Continued)

(52) U.S. Cl.
CPC ....... *A61M 1/1008* (2014.02); *A61B 17/3468* (2013.01); *A61F 2/2427* (2013.01);
(Continued)

(58) Field of Classification Search
CPC .............................. A61M 1/122; A61M 25/09
(Continued)

(56) References Cited

U.S. PATENT DOCUMENTS

| 5,190,050 A | 3/1993 | Nitzsche |
| 5,658,263 A | 8/1997 | Dang et al. |

(Continued)

FOREIGN PATENT DOCUMENTS

| EP | 1534374 B1 | 1/2007 |
| EP | 1807143 A1 | 7/2007 |

(Continued)

OTHER PUBLICATIONS

Sondergaard, Lars et al, First-in-Human Case of Transfemoral CardiAQ Mitral Valve Implantation, Circ. Cardiovasc Interv. 2015.

(Continued)

*Primary Examiner* — Erin M Piateski

(57) ABSTRACT

A system and method used to deliver a percutaneous ventricular assist device (pVAD) or other cardiac therapeutic device to a site within the heart, such as a site at the aortic valve. A flexible device is percutaneously introduced into a vasculature of a patient and positioned to run from a femoral vein, through the heart via a transseptal puncture, and to a femoral artery. The venous-side end of the flexible device is withdrawn out the venous vasculature superior to the heart, and a pVAD is secured to the flexible device. The pVAD is pushed in a distal direction while the arterial-side end of the flexible device is pulled in the proximal direction to advance the pVAD to the target site. A left ventricle redirector aids in orienting the pVAD and preventing migration of the flexible member towards delicate structures of the heart during advancement of the pVAD.

13 Claims, 27 Drawing Sheets

(51) Int. Cl.
  *A61M 1/10*  (2006.01)
  *A61B 17/34*  (2006.01)
  *A61F 2/24*  (2006.01)
  *A61M 25/10*  (2013.01)
  *A61B 17/00*  (2006.01)

(52) U.S. Cl.
  CPC ............ *A61M 1/122* (2014.02); *A61M 1/125* (2014.02); *A61M 25/09* (2013.01); *A61B 2017/00243* (2013.01); *A61B 2017/00327* (2013.01); *A61M 25/10* (2013.01); *A61M 2210/125* (2013.01)

(58) Field of Classification Search
  USPC ......................................................... 600/16
  See application file for complete search history.

(56) References Cited

U.S. PATENT DOCUMENTS

| | | |
|---|---|---|
| 5,873,842 A | 2/1999 | Brennen et al. |
| 6,004,280 A | 12/1999 | Buck et al. |
| 6,183,463 B1 | 2/2001 | Webster, Jr. |
| 6,475,195 B1 | 11/2002 | Voda |
| 6,592,581 B2 | 7/2003 | Bowe |
| 6,613,046 B1 | 9/2003 | Jenkins et al. |
| 7,056,314 B1 | 6/2006 | Florio et al. |
| 7,115,134 B2 | 10/2006 | Chambers |
| 7,481,805 B2 | 1/2009 | Magnusson |
| 7,647,124 B2 | 1/2010 | Williams |
| 7,729,782 B2 | 6/2010 | Williams et al. |
| 8,096,985 B2 | 1/2012 | Legaspi et al. |
| 8,235,916 B2 | 8/2012 | Whiting et al. |
| 8,435,227 B2 | 5/2013 | Takagi et al. |
| 8,606,369 B2 | 12/2013 | Williams et al. |
| 8,827,982 B2 | 9/2014 | Goode et al. |
| 8,926,588 B2 | 1/2015 | Berthiaume et al. |
| 8,996,135 B2 | 3/2015 | Elencwajg |
| 9,072,872 B2 | 7/2015 | Asleson et al. |
| 9,078,994 B2 | 7/2015 | Rosenman et al. |
| 9,173,646 B2 | 11/2015 | Fabro |
| 9,220,874 B2 | 12/2015 | Pillai et al. |
| 9,320,564 B2 | 4/2016 | Avitall et al. |
| 9,511,205 B2 | 12/2016 | Inoue |
| 9,616,197 B2 | 4/2017 | Serina et al. |
| 9,814,814 B2 | 11/2017 | Corbett et al. |
| 10,105,221 B2 | 10/2018 | Siegel |
| 2001/0005789 A1 | 6/2001 | Root et al. |
| 2004/0003819 A1 | 1/2004 | St. Goar et al. |
| 2004/0127847 A1 | 7/2004 | DuBois |
| 2005/0222557 A1* | 10/2005 | Baxter ................... A61B 18/24 606/16 |
| 2006/0089618 A1 | 4/2006 | McFerran et al. |
| 2006/0155158 A1* | 7/2006 | Aboul-Hosn ......... F04D 29/048 600/16 |
| 2006/0167535 A1 | 7/2006 | Johnson |
| 2006/0217794 A1 | 9/2006 | Ruiz et al. |
| 2007/0032850 A1 | 2/2007 | Ruiz et al. |
| 2007/0049906 A1 | 3/2007 | Magnusson |
| 2007/0060914 A1 | 3/2007 | Magnusson |
| 2007/0100299 A1 | 5/2007 | Magnusson |
| 2007/0112422 A1 | 5/2007 | Dehdashtian |
| 2007/0156233 A1 | 7/2007 | Kapadia et al. |
| 2007/0299403 A1 | 12/2007 | Crowe et al. |
| 2010/0114306 A1 | 5/2010 | Lenihan et al. |
| 2010/0160725 A1 | 6/2010 | Kiser et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0249491 A1 | 9/2010 | Farnan et al. |
| 2011/0022057 A1 | 1/2011 | Eigler et al. |
| 2012/0041422 A1 | 2/2012 | Whiting et al. |
| 2012/0101442 A1 | 4/2012 | Legaspi et al. |
| 2012/0172656 A1 | 7/2012 | Walters et al. |
| 2014/0107399 A1 | 4/2014 | Spence |
| 2014/0276395 A1 | 9/2014 | Wilson et al. |
| 2014/0276782 A1 | 9/2014 | Paskar |
| 2014/0276904 A1 | 9/2014 | Hanson et al. |
| 2014/0303719 A1 | 10/2014 | Cox et al. |
| 2014/0371719 A1 | 12/2014 | Carnevale |
| 2015/0258260 A1* | 9/2015 | Tuseth ................ A61M 1/1008 600/16 |
| 2015/0258312 A1 | 9/2015 | Tuseth |
| 2015/0273136 A1 | 10/2015 | Osiev |
| 2015/0305864 A1 | 10/2015 | Quadri et al. |
| 2015/0328382 A1 | 11/2015 | Corbett et al. |
| 2016/0022961 A1 | 1/2016 | Rosenman et al. |
| 2016/0066993 A1 | 3/2016 | Avitall et al. |
| 2016/0074623 A1 | 3/2016 | Pillai et al. |
| 2016/0158506 A1 | 6/2016 | Eliasen et al. |
| 2016/0213472 A1 | 7/2016 | Kim |
| 2016/0220785 A1 | 8/2016 | Fabro |
| 2016/0317288 A1 | 11/2016 | Rogers et al. |
| 2016/0317289 A1 | 11/2016 | Tozzi |
| 2017/0106170 A1 | 4/2017 | Hsueh et al. |
| 2017/0224483 A1 | 8/2017 | Kizuka |
| 2017/0245988 A1 | 8/2017 | Siegel et al. |
| 2017/0258614 A1 | 9/2017 | Griffin |
| 2017/0361065 A1 | 12/2017 | Legaspi et al. |
| 2018/0043132 A1 | 2/2018 | Serina et al. |
| 2018/0078370 A1 | 3/2018 | Kovalsky et al. |
| 2018/0104398 A1 | 4/2018 | Corbett et al. |
| 2018/0280668 A1* | 10/2018 | Alaswad ................ A61M 1/101 |
| 2018/0311421 A1 | 11/2018 | Tuseth et al. |
| 2018/0318079 A1 | 11/2018 | Patel et al. |
| 2019/0117937 A1 | 4/2019 | Humphrey et al. |
| 2019/0151614 A1 | 5/2019 | Hsueh et al. |

FOREIGN PATENT DOCUMENTS

| | | |
|---|---|---|
| EP | 2687254 B1 | 4/2015 |
| EP | 2913080 A2 | 9/2015 |
| EP | 3142721 A1 | 3/2017 |
| EP | 3288491 A1 | 3/2018 |
| EP | 3302363 A1 | 4/2018 |
| WO | 200060995 A2 | 10/2000 |
| WO | 2005037345 A2 | 4/2005 |
| WO | 2006052651 A1 | 5/2006 |
| WO | 2007149974 A2 | 12/2007 |
| WO | 2008012914 A1 | 1/2008 |
| WO | 2009137712 A1 | 11/2009 |
| WO | 2010085456 A1 | 7/2010 |
| WO | 2010085457 A1 | 7/2010 |
| WO | 2012178115 A2 | 12/2012 |
| WO | 2013181397 A1 | 12/2013 |
| WO | 2014065714 A2 | 5/2014 |
| WO | 2014138482 A1 | 9/2014 |
| WO | 2014197962 A1 | 12/2014 |
| WO | 2015175718 A1 | 11/2015 |
| WO | 2016176409 A1 | 11/2016 |
| WO | 2016196933 A1 | 12/2016 |
| WO | 2017139246 A1 | 8/2017 |
| WO | 2017155892 A1 | 9/2017 |
| WO | 1994003227 A1 | 4/2018 |
| WO | 2018098210 A2 | 5/2018 |
| WO | 2019055154 A2 | 3/2019 |

OTHER PUBLICATIONS

International Search Report and Written Opinion for PCT/US2017/062913 dated Feb. 8, 2018.
International Search Report and Written Opinion for corresponding PCT/US2020/017370 dated Nov. 6, 2020.
Office Action dated Oct. 30, 2020 for Related U.S. Appl. No. 16/578,374.
Office Action dated Oct. 1, 2020 for Related U.S. Appl. No. 16/578,379.

* cited by examiner

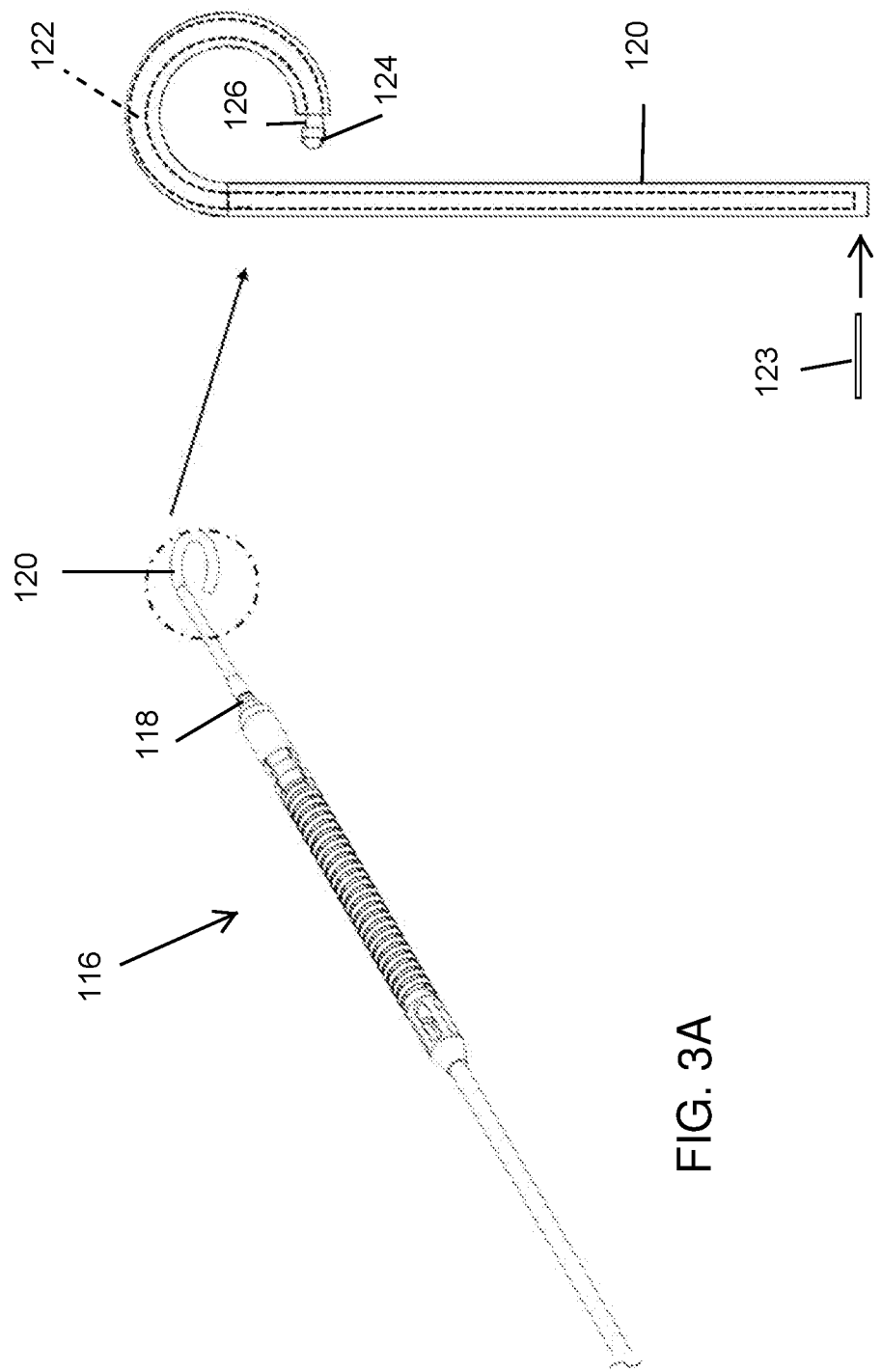

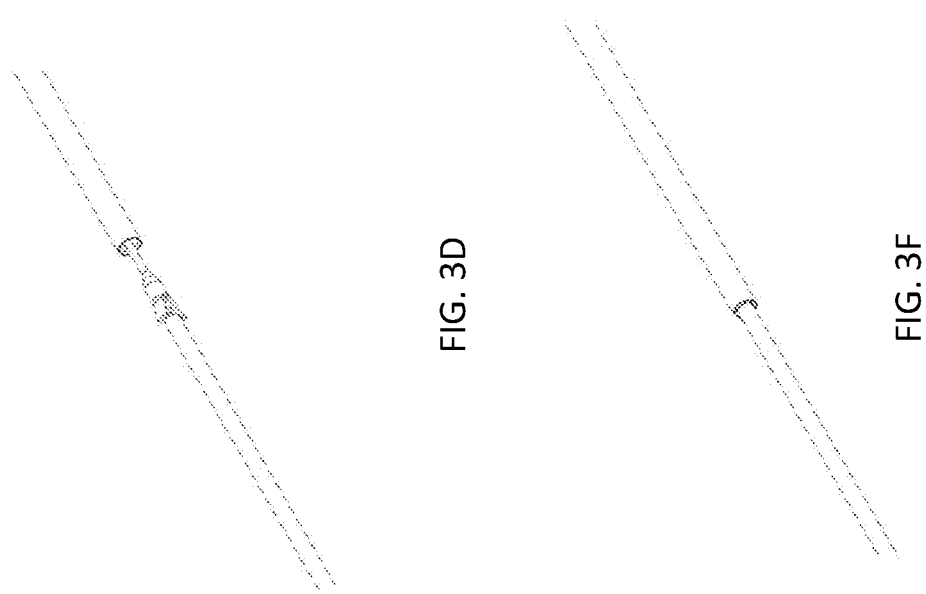
FIG. 3D
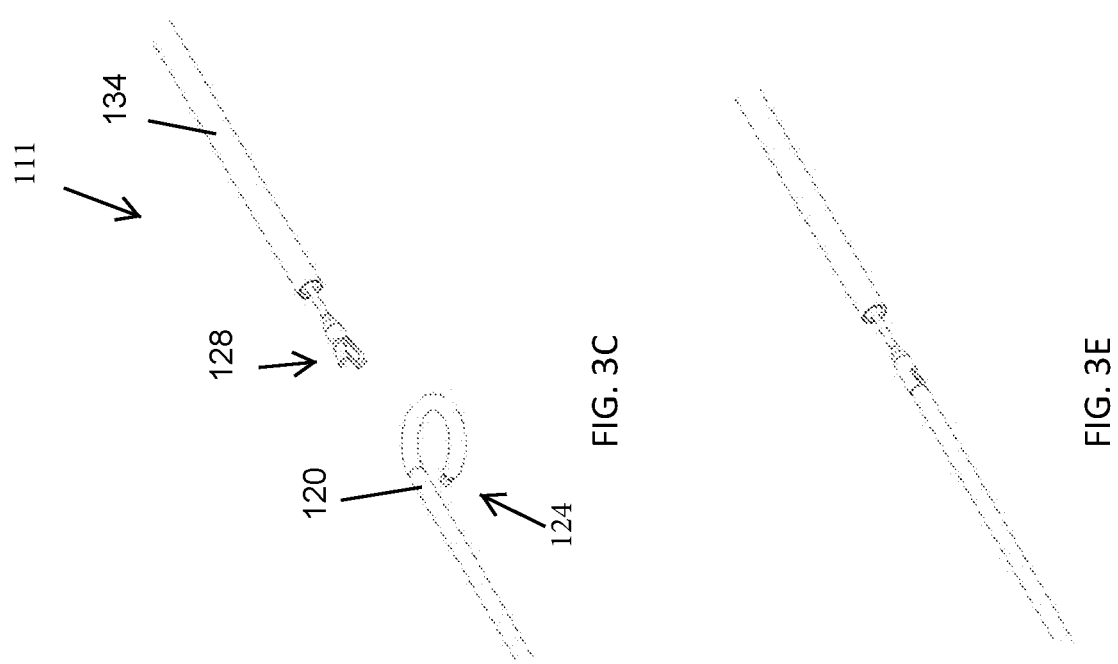
FIG. 3C
FIG. 3E
FIG. 3F

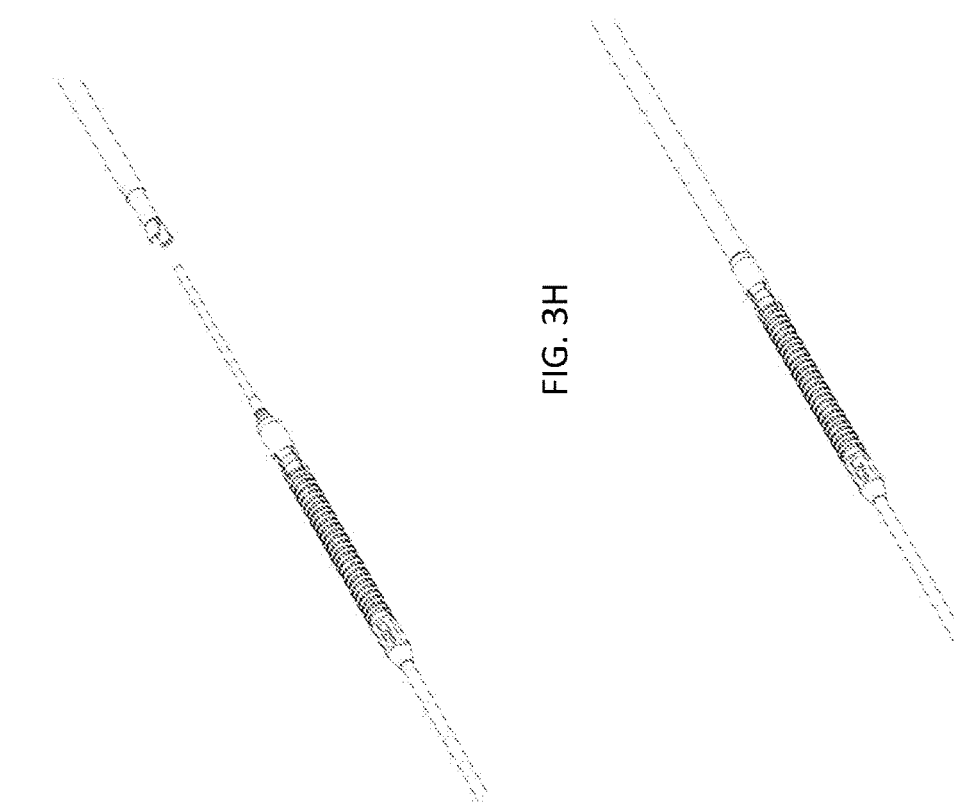
FIG. 3G
FIG. 3H
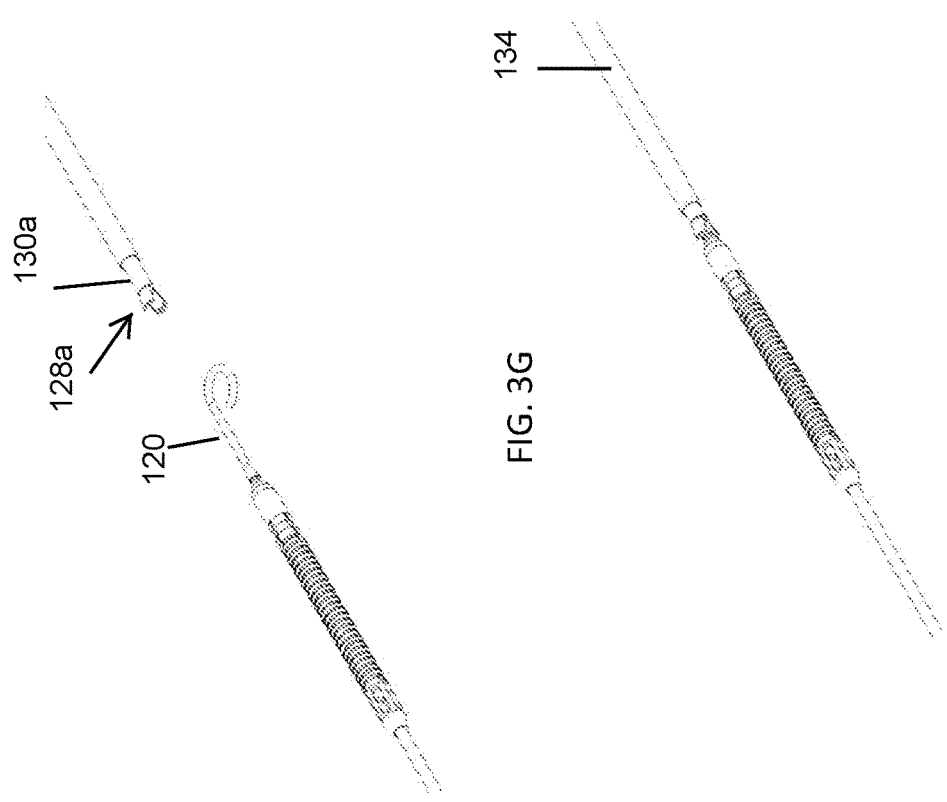
FIG. 3I
FIG. 3J

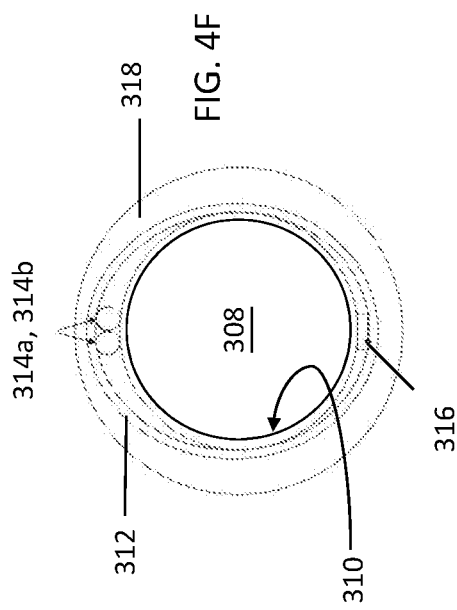
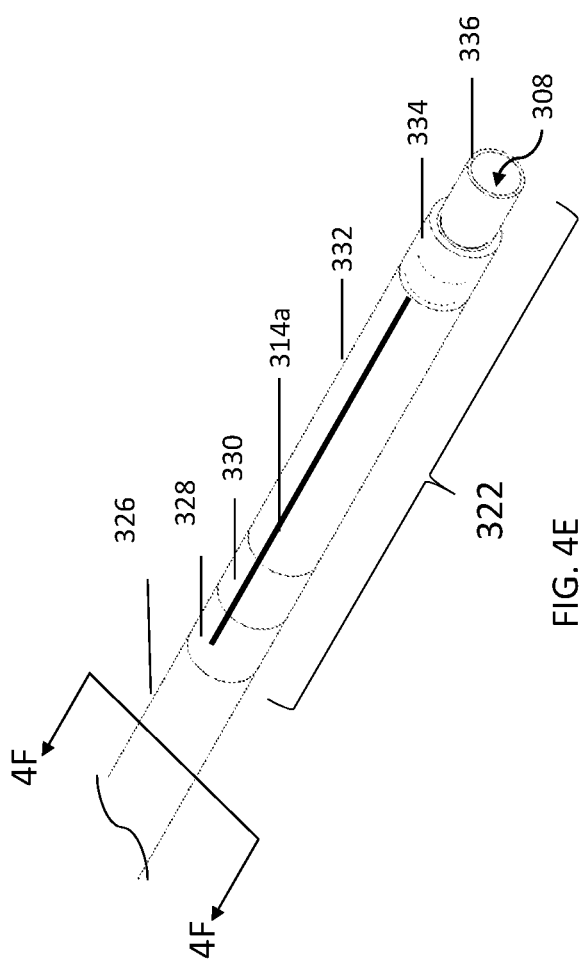

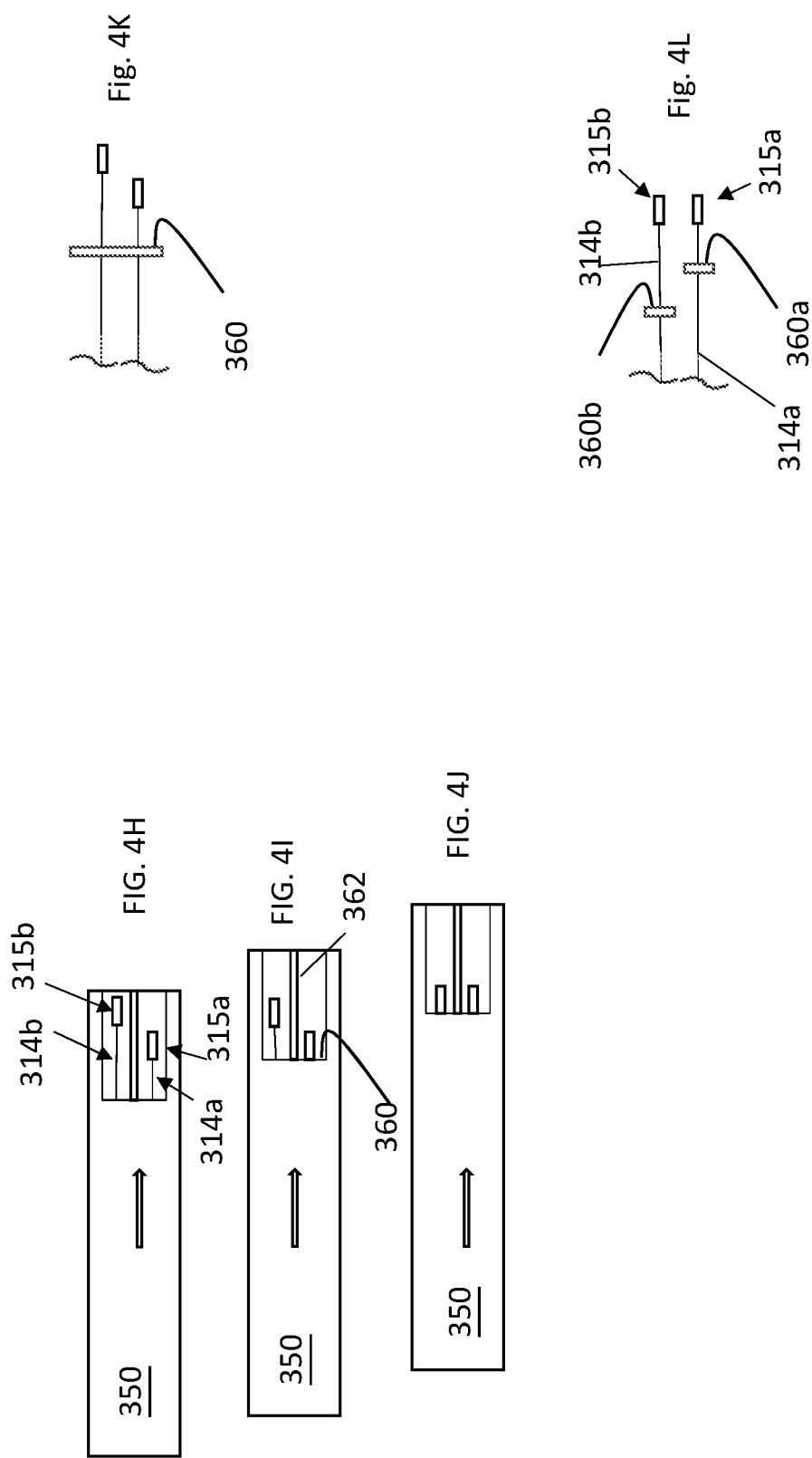

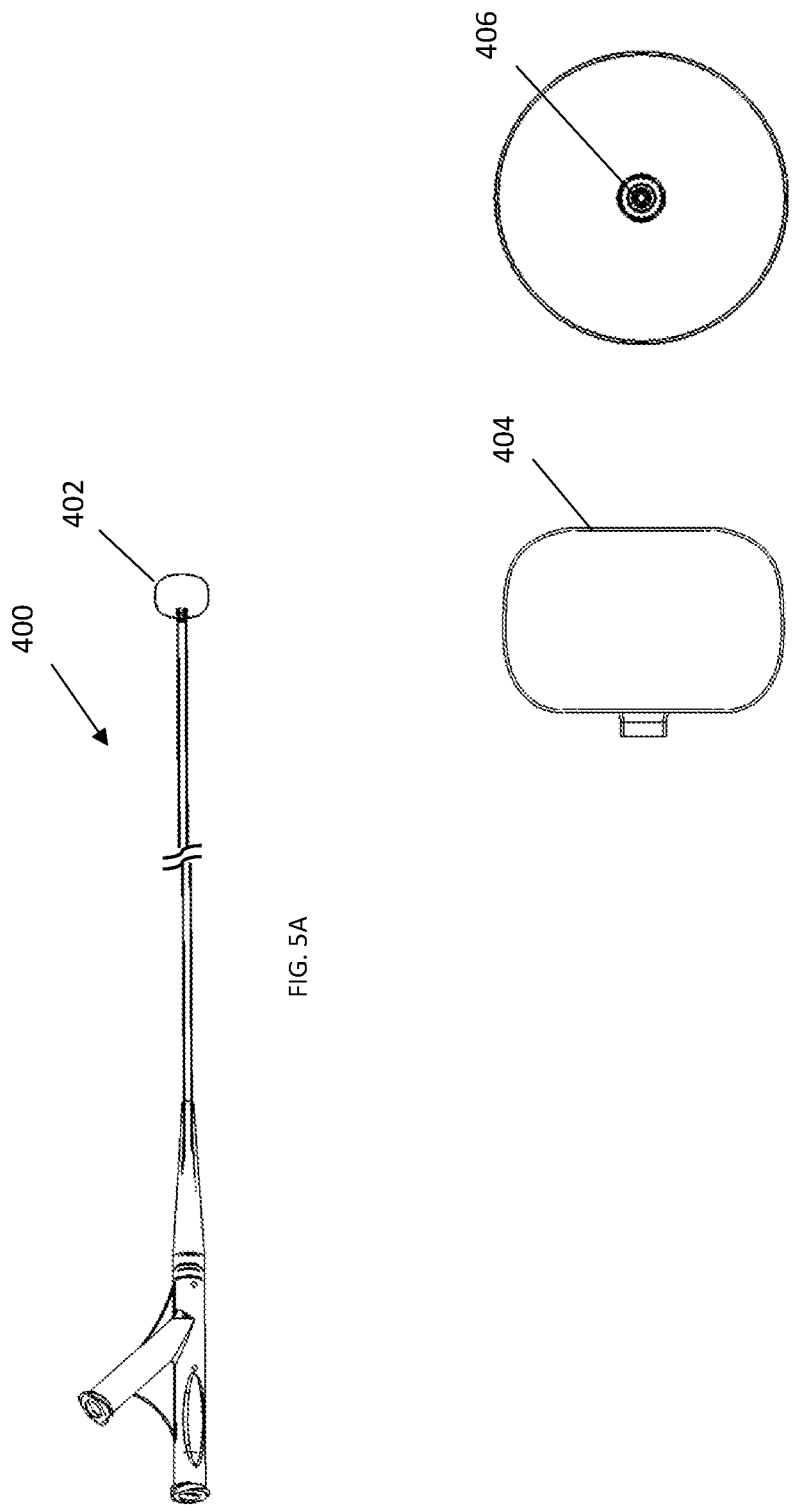

SYSTEMS AND METHODS FOR TRANSSEPTAL DELIVERY OF PERCUTANEOUS VENTRICULAR ASSIST DEVICES AND OTHER NON-GUIDEWIRE BASED TRANSVASCULAR THERAPEUTIC DEVICES

This application claims the benefit of U.S. Provisional Application No. 62/802,212, filed Feb. 7, 2019, which is incorporated hereby reference.

BACKGROUND

Several new types of percutaneous interventional devices have recently been introduced that do not rely on a traditional guidewire for delivery to the heart. These non-guidewire based (NGB) devices include percutaneous ventricular assist devices as well as certain transvascular aortic or mitral valve repair or replacement devices. Percutaneous ventricular assist devices (pVADs) are pump devices positioned within the heart and used for circulatory support. In order for these pVADs to be considered minimally invasive, interventional cardiology-based procedures, they must enter the heart from a percutaneous puncture of a peripheral vessel. If the devices are thin and flexible, they may be introduced in an artery and advanced retrograde across the aortic valve to the left ventricle. If they are too large to enter an artery, they may be introduced into larger peripheral veins but then they must cross from the right side of the heart to the left side across the inter-atrial septum in a well-established but tortuous route via a technique known as transseptal catheterization. However, because of the combined large size and/or rigidity of these high cardiac output pVADS, generally the transseptal route has proven to be extremely difficult. One major obstacle is that pVAD designs generally involve a pump housing on the distal end which would prohibit passage of a traditional guidewire lumen through the housing.

The traditional transseptal approach involves driving a therapeutic device over a 0.035 in. guidewire that has been previously introduced across the interatrial septum, through the left atrium then across the mitral valve and into the left ventricle. This guidewire produces a highly flexible track over which these large devices can potentially be forced into position. However, high cardiac output pVADs are too big and too rigid to easily negotiate the tight bends that are required when crossing into and navigating through the left atrium, left ventricle and the aorta. As a result, they can fail to follow the course of the guidewire and continue in a relatively straight course when attempting to negotiate the multiple turns required, causing both the deformed guidewire and tip of the therapeutic device to protrude into the delicate cardiac tissues.

Commonly owned co-pending application PCT/US2017/62913, filed Nov. 22, 2017 and published as WO/2018/098210 (incorporated herein by reference) discloses a system and method for delivering mitral valve therapeutic devices to the heart (such as devices for positioning a replacement mitral valve or devices for treating a native mitral valve) using a transseptal approach, and describes exemplary methods for using those systems, generally for transvascular devices of a type that are typically delivered over a guidewire, from an inferior venous access point such as the femoral vessels. Commonly-owned co-pending application PCT/US18/45445, filed Aug. 6, 2018, (incorporated herein by reference) discloses a system and method for delivering various cardiac therapeutic devices, including pVADS, to the heart using a trans-septal approach.

The present application discloses improved systems and methods for delivering cardiac therapeutic devices positionable in the heart, particularly at the aortic valve, and particularly pVAD devices as well as other NGB devices, together with exemplary methods for using those systems using superior venous access. Note that while the discussion below focuses on pVAD devices, the described systems and methods can also be used for other NGB cardiac therapeutic devices such as are delivery devices for use in delivering percutaneous mitral valve or aortic valve prostheses to the corresponding valve site within the heart, and/or devices used to repair valves of the heart, such as the aortic or mitral valves, or other devices intended to be used or implanted within the heart.

BRIEF DESCRIPTION OF THE DRAWINGS

FIGS. 1-4F show components of a first embodiment of a conveyor system, in which:

FIG. 3A is a perspective view of an advancer;

FIG. 3B is a side elevation view of the advancer of FIG. 3A;

FIGS. 3C-3F are a sequence of perspective views illustrating engagement of the advancer of FIG. 3B with the grasper of FIG. 2C;

FIGS. 3G-3J are a sequence of perspective views illustrating engagement of an alternative advancer and grasper;

FIG. 4E is a perspective view of the distal tip section of FIG. 4B in the straight position.

FIG. 4F is a cross-section view of the LVR of FIG. 4A, taken along the plane designated 4F-4F in FIG. 4E.

FIGS. 4H-4J are a sequence of drawings schematically illustrating movement of the pull wire slider during activation and locking of the pull wires.

FIG. 4K is similar to FIG. 4J but shows only the pull wires and the engagement feature of the slider.

FIG. 4L is similar to FIG. 4K but shows an alternative configuration of pull wires and engagement features for the slider.

FIG. 5A is a side elevation view of a tracker balloon catheter;

FIG. 5B is a side elevation view of the balloon of the balloon catheter of FIG. 5A;

FIG. 5C is a distal end elevation view of the balloon of FIG. 5B;

FIGS. 6A-15 are a sequence of drawings schematically illustrating use of the system of FIGS. 1-4E in which:

FIGS. 6A and 6B illustrate transseptal catheterization.

FIG. 7 illustrates advancement of the RLC over the wire and use of the RLC to initially assess whether the RLC is free of involvement of the chordae tendinae of the mitral valve;

FIG. 8 illustrates use of a modified tracker balloon catheter for atrial septostomy and to assess whether the wire is free of involvement of the chordae tendinae of the mitral valve;

FIG. 9 illustrates the RLC after it has been advanced over the wire to the descending aorta, and advancement of a snare over the RLC in the descending aorta;

FIG. 10 shows the cable having replaced the wire through the RLC, and use of the snare to withdraw the cable from the right femoral artery;

FIG. 11 shows the system with the cable extending from the right femoral vein to the right femoral artery, and the RLC extending from the right femoral vein to the descending aorta. It further shows the LVR being advanced over the cable and positioned in the descending aorta just prior to making contact with the RLC;

FIG. 12 shows the system following removal of the RLC through the right femoral vein after distal end of the LVR has been positioned in the left ventricle and after the venous-side end of the cable has been withdrawn from the right subclavian vein. The grasper is shown as it is about to be engaged to the cable at the right femoral artery, FIG. 13 depicts the grasper and LVR after the grasping end of the grasper has been retrieved at the right subclavian vein and the LVR has been advanced to the LV after it has been advanced through the aortic arch and aortic valve in tandem with the RLC as the tips of the two catheters are pressed together in order to provide a smooth continuous surface to facilitate passage through these structures. The pVAD is also shown as it is prepared to be engaged by the grasper;

FIG. 14 shows the pVAD passing through the mitral valve as it is pushed from the right subclavian vein and also pulled by the grasper. The LVR is deployed in the left ventricle; its distal tip is receiving the grasper tip and advancer;

FIG. 15 shows the pVAD in position in the aortic valve. The grasper cable has released the advancer component of the pVAD and the LVR and grasper cable have been removed via the arterial sheath.

DETAILED DESCRIPTION

The presently disclosed system is designed to aid in the delivery of a pVAD or other NGB cardiac therapeutic devices to a location within the heart, such as at the aortic valve.

As will be appreciated from a review of the more detailed discussion that follows, rather than simply pushing a non-steerable pVAD over a guidewire or relying on a bend of the delivery device from behind the housing with pull wires, as with the conventional approach discussed in the Background, the presently disclosed system directly steers the pVAD delivery system and guides it forward from the front of the device. This unique approach gives greater control over the movement of the pVAD into and through the heart. It includes components that allow the user to both push the proximal end of the pVAD while simultaneously pulling and directly steering on the distal tip of it with equal and coordinated force to drive the pVAD safely across the interatrial septum and through the heart. Features of the system specifically apply a strong steering force that draws the distal nose of the pVAD medially and inferiorly away from protrusion into delicate cardiac tissues. This force directs the stiff, bulky pVAD into position across the interatrial septum, into the left atrium and into position for deployment in the aortic valve ring. As it crosses the left atrium and mitral valve ("MV"), the pVAD is positioned precisely in the center of the valve at an angle that is perpendicular to the MV plane by use of a unique bridging guy wire steering mechanism present in a device referred to as the left ventricular redirector or "LVR." (described in detail below). By directly steering the pVAD from the front, the LVR not only keeps the pVAD away from the delicate structures of the left atrium, mitral valve and apex of the left ventricle, but also avoids mitral regurgitation as the pVAD traverses the MV during pVAD placement.

In the description of the system and method below, the access points for the components of the system are described as the right femoral vein ("RFV") and the right subclavian vein ("RSV") for the venous access and the right femoral artery ("RFA") for the arterial access. However, the system and method can just as readily be used with a different combination of venous and arterial access, including the left femoral vein and artery ("LFV", "LFA"), left subclavian vein, or the right or left internal jugular vein.

First Embodiment—System

FIGS. 1-4A illustrate components that collectively comprise a first embodiment of a conveyor system suitable for use in moving a pVAD intravascularly from a percutaneous entry position (e.g. a position superior to the heart such as the RSV) and then into, and through, the heart to its ultimate position within the heart. Further details concerning each of the illustrated components may be found in the various co-pending patent applications referenced in this section, each of which is incorporated herein by reference.

Right-to-Left Conduit

Figure 1A:
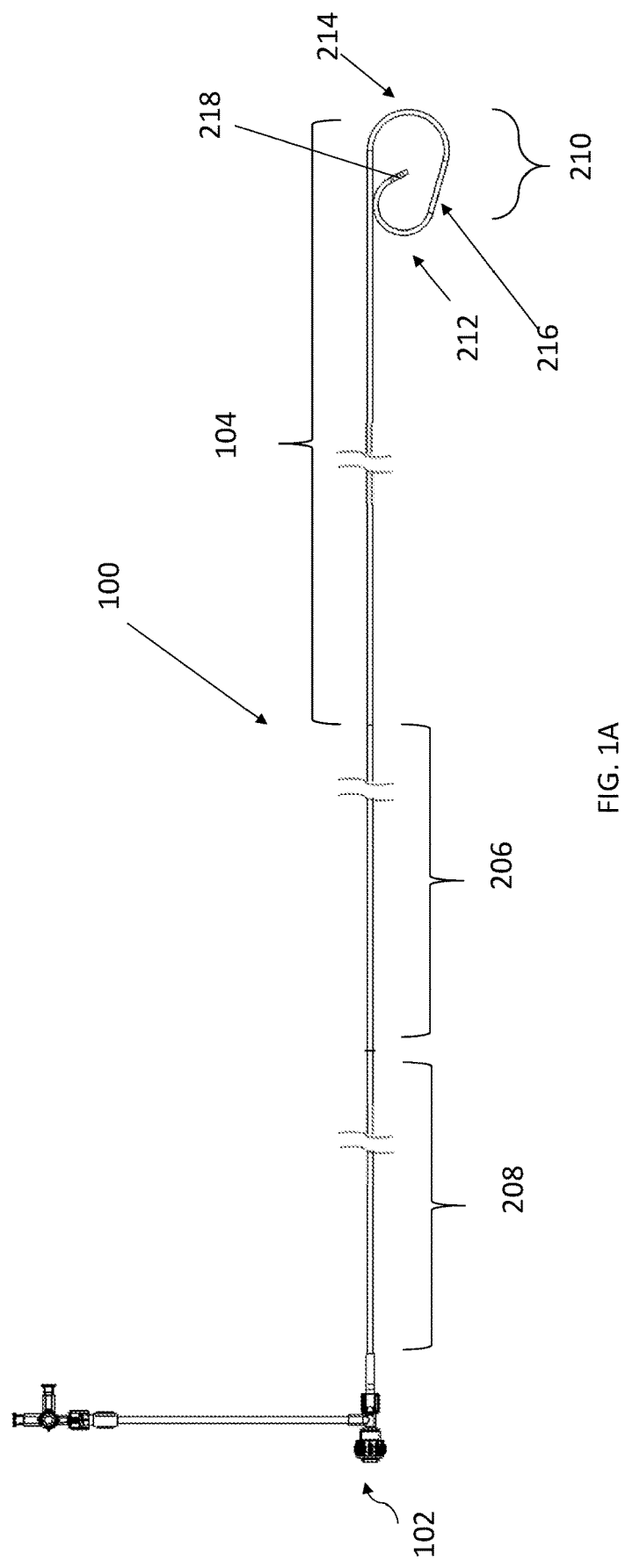
FIG. 1A is a side elevation view of a Right-to-Left conduit ("RLC")

Referring to FIG. 1A the system includes a Right-to-Left conduit 100 ("RLC"), an elongate tubular catheter having a length sufficient to permit it to extend from the RFV of a human adult to the right atrium, across the interatrial septum (via a trans-septal puncture) to the left atrium, through the mitral valve, left ventricle, aortic valve to the aortic arch, and then to the descending aorta. In a preferred embodiment, this length exceeds 150 cm, and it may be 160 cm or longer.

A lubricious lumen extends through the RLC 100 from a proximal port 102 to an opening at the distal end 104. A flush port is also fluidly connected with the lumen of the RLC as shown. The RLC 100 is used to aid in the passage of other system components from the venous vasculature through the heart (including through a transseptal puncture) to the arterial vasculature, so that they can be used to deliver the pVAD. Its distal portion 104 is shape set into a curved configuration which, as discussed in application Ser. No. 16/578,374, entitle Conduit for Transseptal Passage of Devices to the Aorta, filed Sep. 22, 2019, helps the distal end of the RCL pass into the mitral valve after it has crossed the intra-atrial septum from the right to the left side of the heart, and aids in orienting the distal opening of the RLC towards the aortic valve when the distal part of the RLC is in the left ventricle. This allows devices passed through the RLC to move safely into the aorta as will be better understood from the discussion of the method steps relating to FIG. 7.

Proximal to the distal portion 104 are an intermediate portion 206, and a proximal portion 208. The proximal and intermediate portions, 208, 206 and much of the distal portion 104, are of generally straight tubular construction. These parts of the shaft may be collectively referred to as the main body of the shaft. The distal portion 104 includes a distal loop 210 that has been shape set. The shape of the loop helps the distal end of the RCL pass into the mitral valve after it has crossed the intra-atrial septum from the right to the left side of the heart, further aids in orienting the distal opening of the RLC towards the aortic valve (as will be discussed in connection with the method below) when the distal part of the RLC is in the left ventricle.

More particularly, the distal loop 210 includes a distal (where for the purposes of this description of the curves of the RLC the term "distal" and "proximal" are used in regard to the entire length of the catheter) curve 212, a more proximal curve 214, a generally straight segment 216 extending between the curves, and a distal tip 218. The RLC is shape set with the longitudinal axes of the distal and proximal curves in a common plane, although in alternative embodiments they might lie in different planes. In other embodiments, one or both of the curves might be formed with a shape where the longitudinal axis forms a three-dimensional shape and thus does not lie within a single plane. The generally straight segment 216 may be straight or it may be curved with a very large radius of curvature to produce a significantly more gradual curve than the proximal and distal curves.

The curves 212, 214 are arranged to cause the distal loop 210 to curve back on itself, so that the distal curve 212 is formed by a part of the RLC shaft that is closer along the length of the shaft to the distal tip 218 than is the proximal 1 curve 214. The radius of the distal curve is smaller than that of the proximal curve, so that the lateral width (perpendicular to the longitudinal axis of the straight section of the shaft) of the loop 210 tapers inwardly from a proximal to distal direction. The distal tip is preferably enclosed within the loop, bounded by distal and proximal curves, segment 216, and the main body of the shaft. It is also, preferably, oriented with its distal opening facing away from the main body of the shaft.

Figures 1B, 1C:
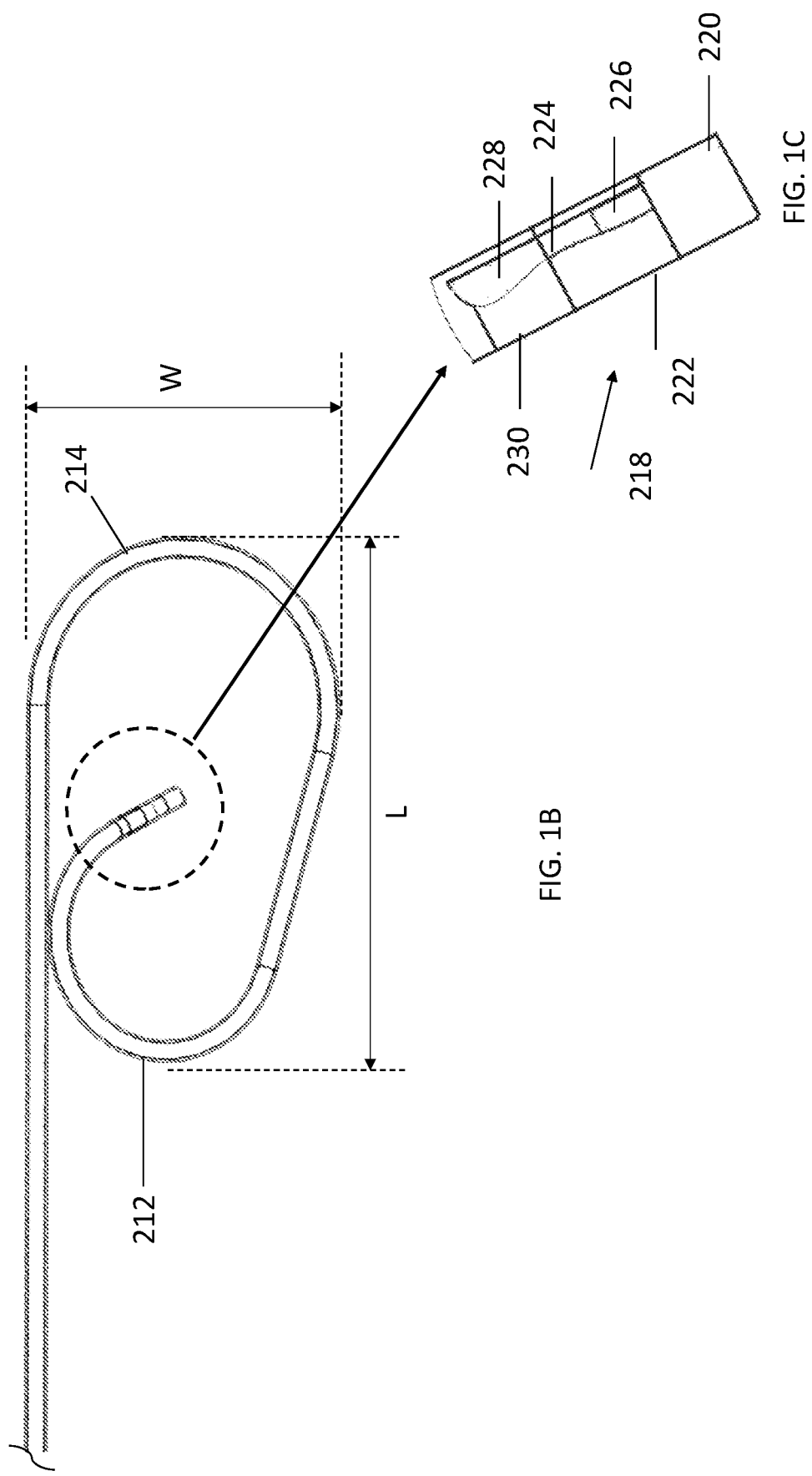
FIG. 1B is a side elevation view of the distal part of the RLC shown in FIG. 1A.
FIG. 1C is a partially cut-away view of the region of the RLC encircled in FIG. 1B.

Referring to FIG. 1B, the radii of the distal and proximal curves, the length of the generally straight segment 216 along its longitudinal axis, the widest lateral dimension W of the distal loop (measured in a direction perpendicular to the longitudinal axis of the straight part of the RLC), and the longitudinal length L of the distal loop (in a direction parallel to the longitudinal axis of the straight part of the RLC) are proportioned so that when the proximal curve 214 is within mitral valve, the distal 1 curve 212 is positioned in the left ventricular outflow tract (as shown in 1D) and the tip 218 is oriented towards, and in close proximity to, the aortic valve. In one embodiment, length L may be in the range of 65-95 mm, with a preferred range of approximately 70-90 mm, or more preferably approximately 75-85 mm. Width W may be in the range of 35-65 mm, with a preferred range of approximately 40-60 mm, or more preferably approximately 45-55 mm. The radius of the proximal curve 212 may be in the range of 5-35 mm, with a preferred range of 10-30 mm, and a most preferred range of 15-25 mm. The radius of the distal curve 214 may be in the range of 10-40 mm, with a preferred range of 15-35 mm, and a most preferred range of 20-30 mm.

Figure 1D:
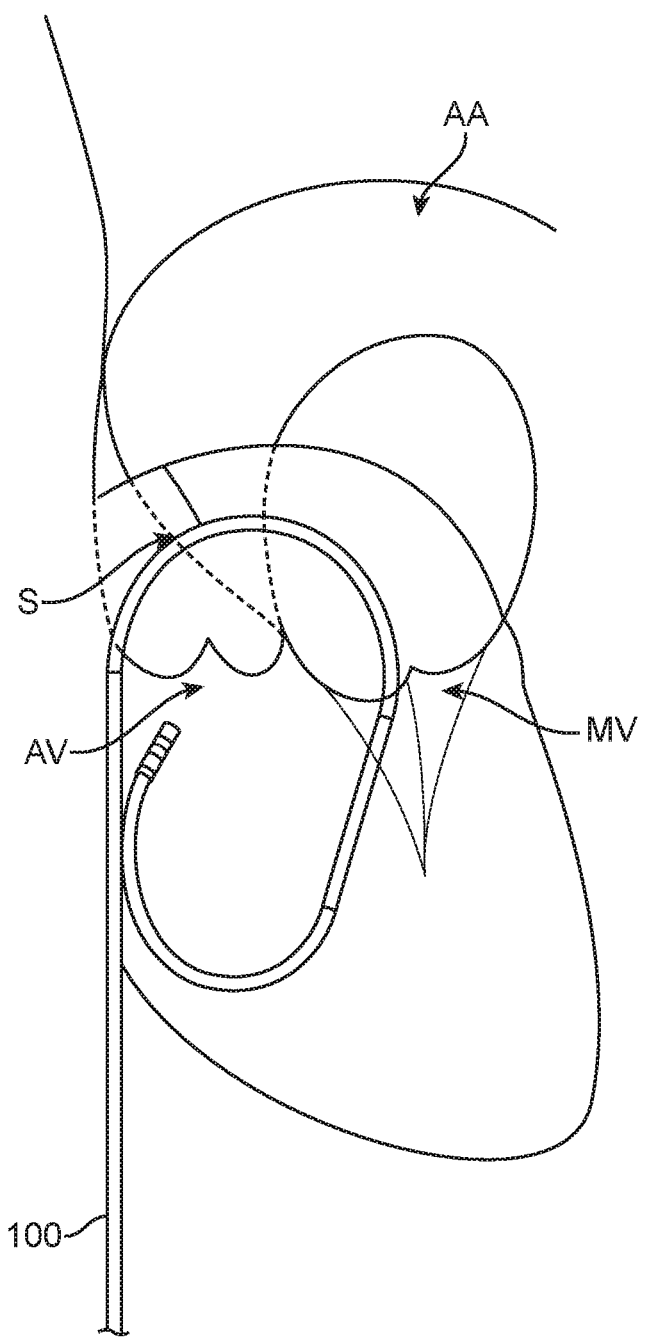
FIG. 1D schematically illustrates the RLC positioned with its distal end in the left ventricle with its distal tip oriented towards the aortic valve.

In the embodiment that is shown, the widest lateral dimension of the proximal curve 214, taken in a direction perpendicular to the longitudinal axis of the main shaft of the conduit, is wider than the widest lateral dimension of the distal curve 212 taken in a direction perpendicular to the longitudinal axis of the main shaft of the conduit. However, in other embodiments these widths may be approximately equal, but the curvature would be ideally selected to orient the distal tip 218 towards the interior of the loop, thus ensuring that when the RLC is positioned with its distal tip in the left ventricle, the tip is generally oriented towards the aorta as shown in FIG. 1D. It should also be recognized that, while generally maintaining the regional durometers resulting from the descriptions above, a steerable tip that employed pull wires could allow a range of tip angles that would ensure orientation towards the aorta for treating hearts of different sizes and shapes as may occur in patients with congestive heart failure.

The circumference of the distal curve 212 passes closely adjacent to the straight section of the main body of the main shaft in distal region 104, so that the main body extends tangentially with respect to the circumference of the distal curve. The curvature of the distal curve continues beyond this tangential area, so that the distal tip 218 is disposed within a generally enclosed loop as noted above. In other embodiments, the proximal curve and/or the distal tip may cross the straight section of the shaft.

The materials for the RLC are selected to give the conduit sufficient column strength to be pushed through the vasculature, torqued to orient its tip towards the aortic valve, and tracked over a wire, and it should have properties that prevent the distal loop 210 from permanently deforming as it is tracked over a wire. Although the distal loop 210 is moved out of its pre-shaped loop configuration to track over the wire, it is important that the shape-setting of the curves be retained. Otherwise the performance benefits of the distal loop's shape which, as evident from the Method description below are to aid proper movement into and through the mitral valve, to orient the tip of the RLC towards the aortic valve, and to track over the wire all the way to the descending aorta will not be realized.

Preferred material properties for the RLC will next be given, although materials having different properties may be used without departing from the scope of the invention. The shaft includes an outer jacket formed of suitable polymeric material (e.g. polyether block amide, "PEBA," such as that sold under the brand name Pebax). A wire braid extends through shaft portions 208, 206 and most of 104 to enhance the torqueability of the RLC. A lubricious liner made using PTFE, ultra high molecular weight polyethylene (UHMWPE), or like material also extends through these sections, allow smooth relative movement between the RLC and the wire and cable that pass through it. The braid and liner terminate in the distal tip 218 as will be described with respect to FIG. 1C. The liner, braid and outer jacket are preferably subjected to a reflow process to create a composite material.

The most proximal portion 208 of the RLC, which may be between 450 and 550 mm in length (most preferably between 485 and 525 mm), is preferably formed from a relatively stiff material made from, as one example, 72D Pebax. Adjacent to the proximal portion 108 is the intermediate portion. This portion may have a length between 500-600 mm (most preferably between 530-570 mm), and it is preferably formed of fairly stiff material, but one that is more flexible than that used for the most proximal portion. As one example, this material may be 55D Pebax. These materials give the proximal and intermediate portions 208, 206 sufficient column strength and torqueability needed for its intended use.

Shaft section 104 is designed to be more flexible that the more proximal sections, because it must be able to pass through the heart during use. This section may be formed of a material such as 40D Pebax, although it is more preferably formed of a blend of 40D and 55D Pebax. This avoids an abrupt transition at the junction between sections 104 and 206 and can help to avoid kinking at that junction. The ratio of 40D to 55D material in the blend may be 50:50 or an alternative ratio. Shaft section 104 makes up the most distal part of the straight section of the main shaft, as well as both the distal and proximal curves 214, 212. The length of shaft section 104 is preferably between 510 and 610 mm, and more preferably between 540 and 580 mm.

A preferred configuration for the distal tip 218 will next be described. Referring to FIG. 1C, which is partially cut away to show features below the outer extrusion, the distal tip 218 includes an atraumatic distalmost section 220 formed of soft 35D Pebax or similarly soft material. Just proximal to the distalmost section is a more rigid section (e.g. 55D Pebax) 222, which includes a radiopaque marker band 224 (e.g. PtIr) and the distalmost part of the lubricious liner 226. In the next most proximal section 230 is the terminal portion of the braid 228, which is covered by a more rigid material such as 72D polyethylene or similar material. Each of the sections 220, 222, 230 is very short in length, and preferably between 2-4 mm. As shown, the distal tip is preferably a generally straight section of the RLC extending from the distal curve 212.

It should be pointed out that while a number of preferred features for the RLC have been described above, alternative embodiments of the RLC might use any sub-combination of the above-described features alone or with other features not described here.

Figure 9:
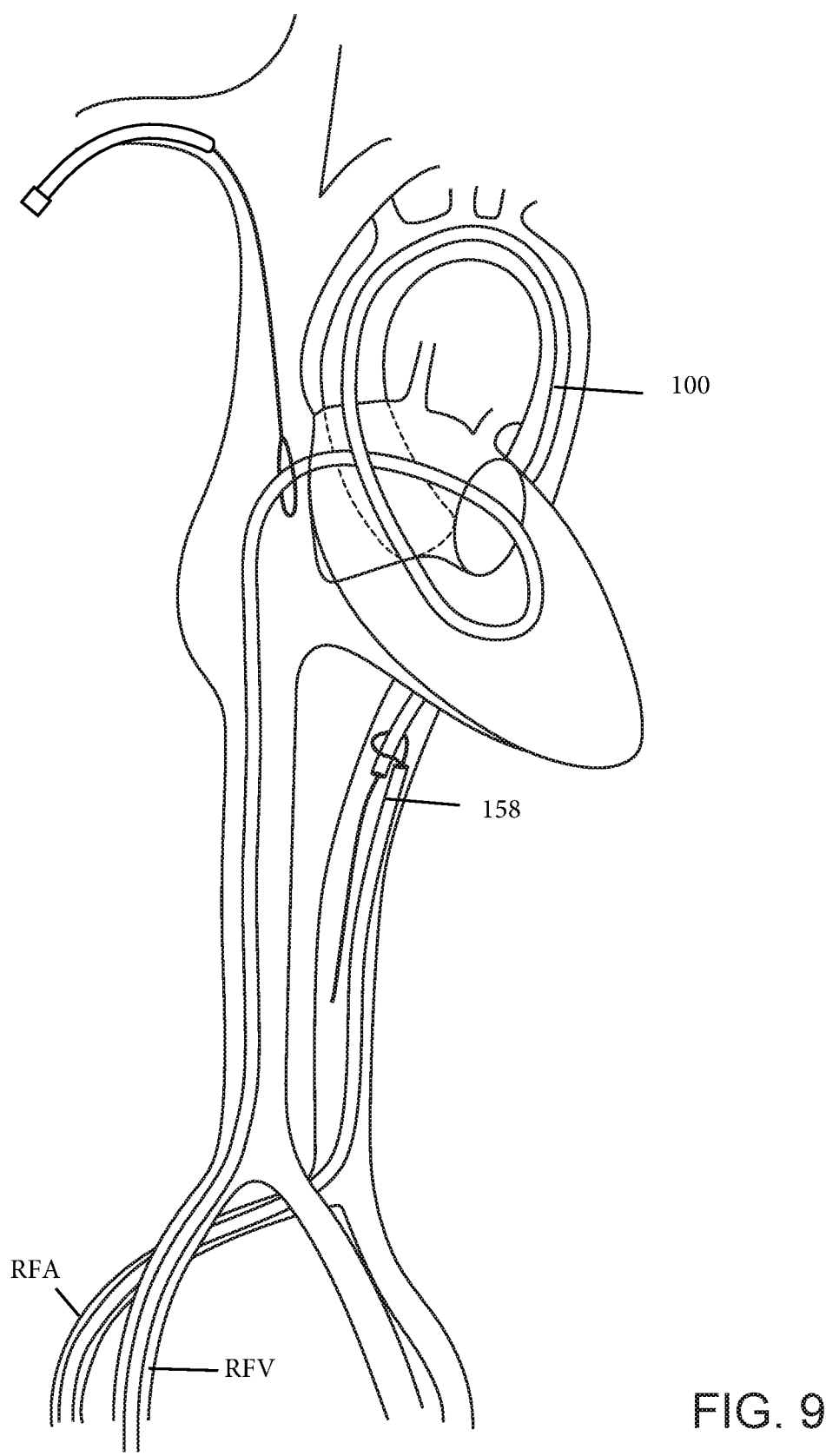
Figure 10:
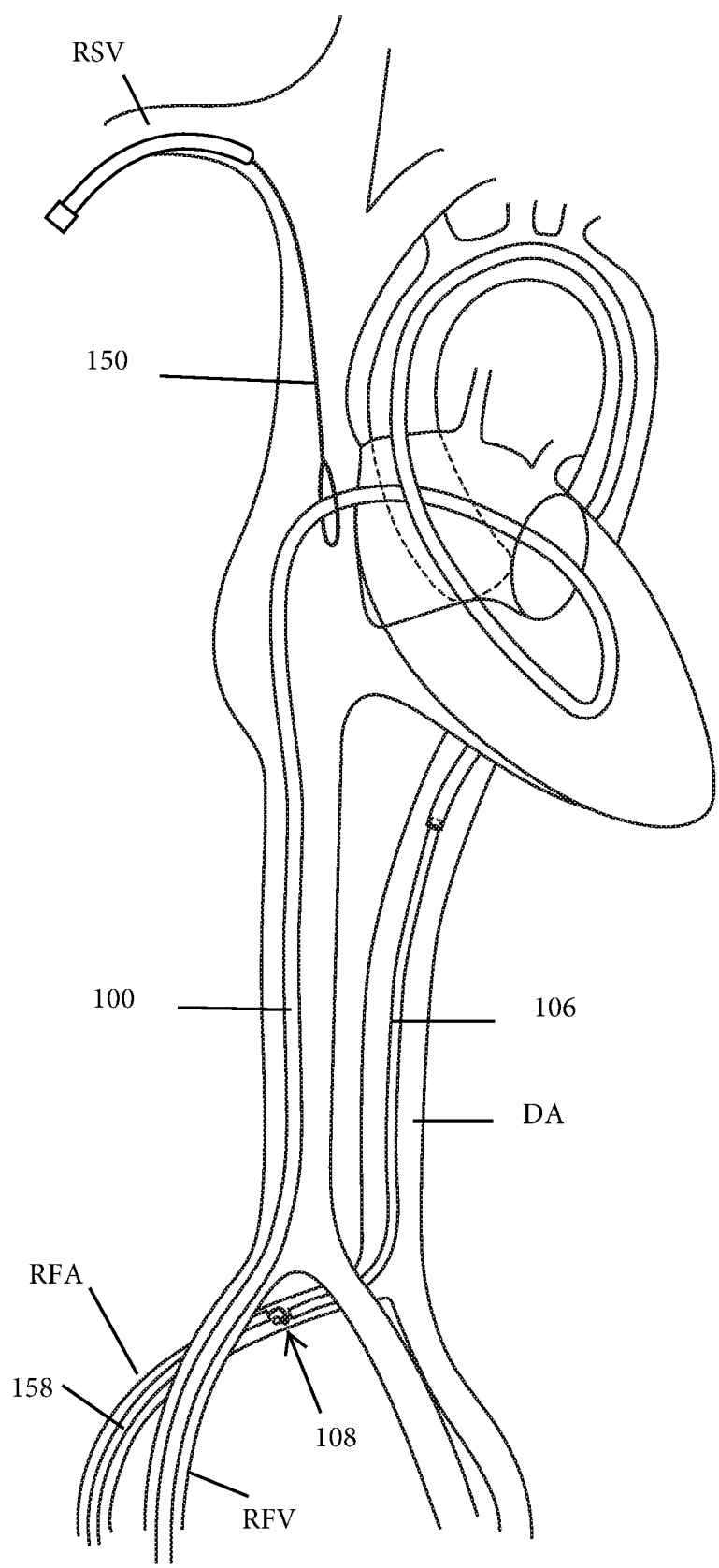

It will be further understood from the description of FIGS. 9 and 10 that in preferred methods of using the system, the RLC is advanced from this position across the aortic valve and into the aorta, establishing a conduit between the venous and arterial vasculature. This conduit is used as a guide for a cable that is to be positioned between the venous and arterial vasculature as discussed below.

While the term "straight" is used to refer to the shape of portions of the RLC in some embodiments, it should be pointed out that the catheter's inherent flexibility may cause it to bend under forces of gravity when held upright, or to curve when tracked over a curved cable or wire, or advanced into contact with another structure. The term "straight" thus should not be used to interpret this application or the corresponding claims as requiring the portion described as being "straight" to hold a straight shape when subjected to gravity or forces from another structure.

In alternative embodiments the distal tip of the RLC may be steerable using pullwires or alternative means, although in preferred embodiments the RLC is not steerable but instead its unique shape is relied on to cause it to pass from the left atrium through the mitral valve to the left ventricle, and to then orient its distal tip towards the aortic valve. While this basic shape configuration is consistent, the various angles so created can be expanded or compressed to various degrees to accommodate cardiac chambers of different sizes by use of guidewires of varying stiffness within the RLC. Stiffer guidewires resulting in more expanded angles and more flexible guidewires resulting in more compressed angles. Even in these cases the regional durometers created by the materials described above in the different regions of the RLC are maintained.

Conveyor Cable

Figure 2B:
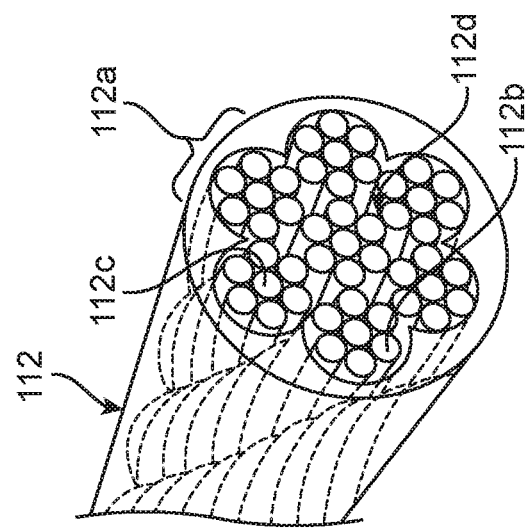
FIG. 2B is a cross-section view of the conveyor cable taken along the plane marked 2B-2B in FIG. 2A.

The system further includes a pVAD conveyor cable 106, shown in FIG. 2. The conveyor cable 106 comprises an elongate cable 112 having a first end with a first engageable feature 108 and a second end with a second engageable feature 110. The cable 112 is preferably made of a wire rope as shown in FIG. 2B. The wire rope includes a plurality of strands 112a, each of which is formed of a plurality of individual wires 112b helically wound around a core 112c (which itself may be a wire). One wire of a strand 112a may comprise a core about which the other wires are wound as shown. Additionally, the wire rope itself has a core 112d about which the strands 112a are helically wound. In this particular example, the core 112d has the same or similar construction as a strand 112c. In alternative embodiments, the cable may instead be manufactured of stainless steel braid or another suitable material or construction having the column strength to be advanced through the RLC when pushed, and the tensile strength to be able to pull the grasper device through the vasculature when pulled, as described below.

The cable is of sufficient length to extend from the right femoral vein (RFV), through the heart via transseptal puncture, through the mitral and aortic valves, and through the aorta to the right or left femoral artery (RFA, LFA) of an adult human.

At different points during the course of a method of delivering a pVAD using the disclosed system, one end of the conveyor cable 106 or the other is captured and/or securely engaged by another component of the system, such as a snare, grasper or other engagement device. For this reason, each engageable feature 108, 110 is designed so that it can be engaged using the engagement device provided for that purpose. These features 108, 110 may be identical or they can have different designs and, as will be understood from the other parts of this specification, the engagement devices used to engage the features 108, 110 may have the same or different configurations. For example, feature 108 may be designed to be captured by a snare within the vasculature (as will be discussed in connection with FIG. 10) and securely engaged by a grasper device at another point in the procedure (FIG. 11), and feature 110 may be designed to be captured by a snare within the vasculature at one point in the procedure (discussed in connection with FIG. 12).

Figure 2A:
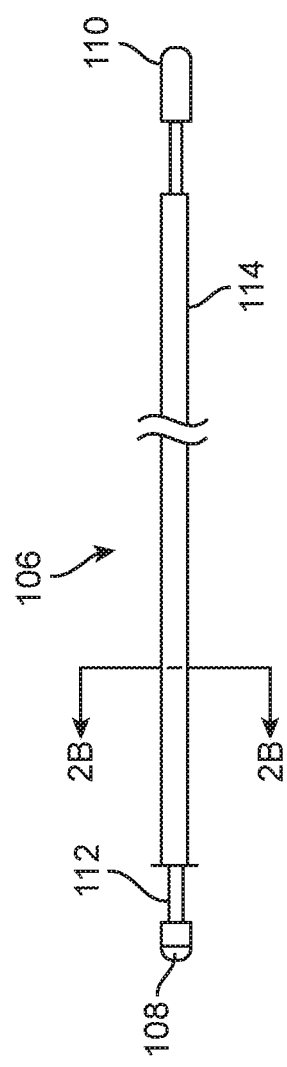
FIG. 2A is a side elevation view of a conveyor cable.

In the embodiment shown in FIG. 2A, the engageable features 108, 110 are tip elements integrally positioned on opposite ends of the length of cable 112. Tip elements may take a variety of different forms. Those shown in FIG. 2A each include a distal face having convex curvature and a cylindrical proximal part with a generally flat proximal face that facilitates engagement using a snare or grasper jaws. Since two ends of a single cable are being discussed, in this specific context, the term "distal" is used to refer to the area at which an end of the conveyor cable 106 terminates, and "proximal" is used to mean longitudinally inset from the corresponding distal end. The cable 112 has a smaller diameter than the tip elements 108, 110. A lubricious polymer coating 114 (e.g. PEBA) covers the cable 112, leaving a gap between each end of the coating and its adjacent tip element 108, 110. This allows room between the tip element and coating 114 for an engagement device such as a snare or grasper jaw to seat when engaging the tip element.

pVAD Advancer

An example of a pVAD 116 is shown in FIG. 3A. Details concerning the operative components of the pVAD, such as its intake and output ports, pump mechanism etc., will not be described as these are known in the art. A common feature of a pVAD device is a highly flexible pigtail element typically formed of a tubular extrusion. The pigtail element extends from the distal nose 118 of the device and is designed to prevent the distal nose from causing trauma to the surrounding tissue. In a pVAD to be implanted using the disclosed system, a modified pigtail, referred to as an advancer element 120, is used. This element has the pigtail shape of the typical pigtail included on many pVAD devices, but it differs from the typical pigtail in multiple ways. First, the advancer element 120 includes a shape memory (e.g. nitinol) element 122 extending through the pigtail (which may be a polymeric extrusion). The nitinol element may have a uniform diameter as shown, or it may have a diameter that tapers inwardly from its proximal end to its distal end to avoid kinking near the junction between the element 122 and the distal nose 118 of the pVAD. A pin 123 (FIG. 3B) may extend laterally through the extrusion of the pigtail and through the distal nose 118 of the pVAD (FIG. 3A) to secure the pigtail to the nose. The pin preferably does not extend through the nitinol element, thus leaving the nitinol element floating unsecured within the extrusion. As is known to those skilled in the art, welding nitinol to stainless can produce a brittle joint between the two materials. This attachment technique allows use of nitinol in the advancer element while ensuring a secure connection between the advancer element and the pVAD 116. Second, the advancer element 120 includes an engageable feature 124 at its distal tip. The engageable feature 124 of the pVAD is configured to be securely engaged by an engagement device such as a snare, grasper, or alternative engagement device.

In a slightly modified embodiment, the nitinol element 122 includes a through hole, and the device is assembled with the pin 123 extending through the outer jacket, the nitinol element 122, and the distal nose of the pVAD.

In the FIG. 3B embodiment, the engageable feature 124 comprises a tip element at the end of a smaller-diameter shaft 126 extending from the lumen of the pigtail's tubular extrusion. It includes a distal face with convex curvature, and a cylindrical proximal part with a generally flat proximal face that facilitates engagement using a snare or grasper jaws. The tip element and shaft may form part of an insert that is inserted into the distal end of the pigtail's lumen and secured in place using adhesive, heat treatment, a threaded engagement, and/or other means. The circumference of the part of the insert that is within the lumen may have threads or a roughened surface to enhance adhesion between the insert and the interior of the lumen.

The tip element shown is one example of a type of engageable element for the advancer. Others might include holes, recesses or grooves that receive corresponding pins, teeth, detents, wires, etc. of the engagement device.

Figure 13:
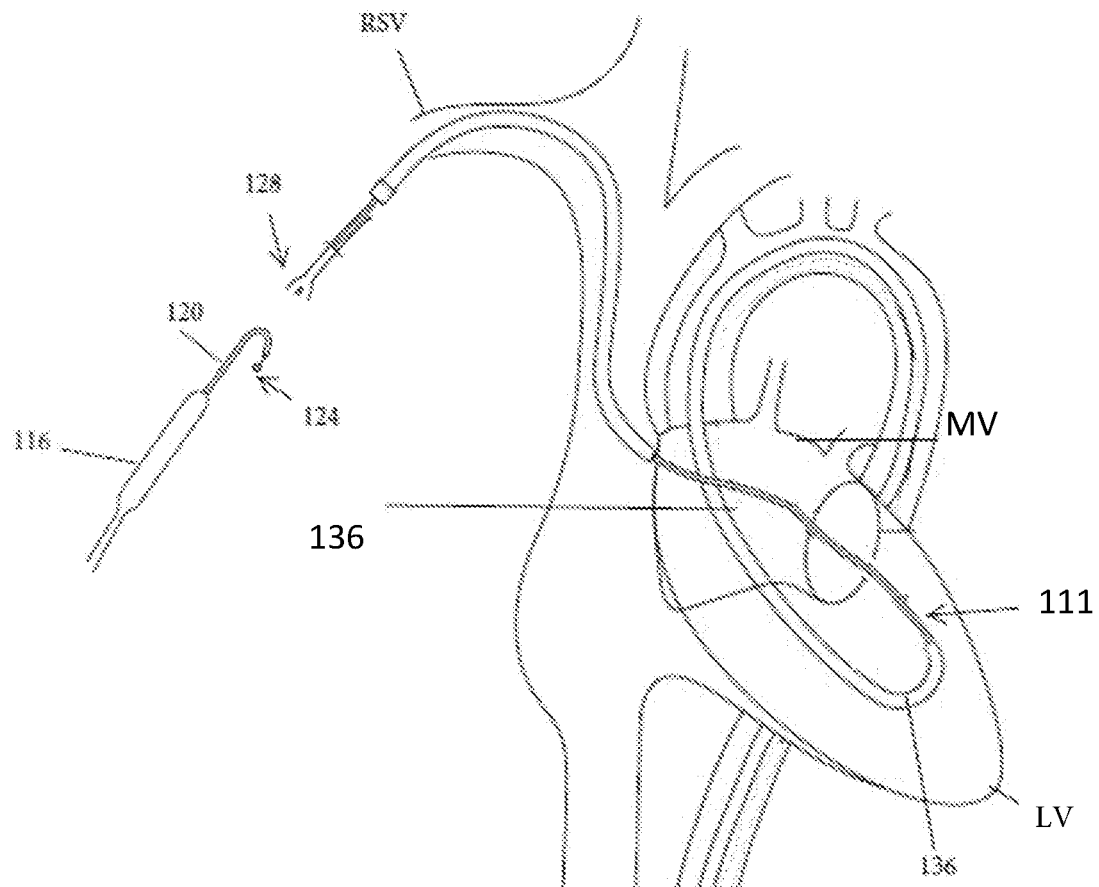
Figure 14:
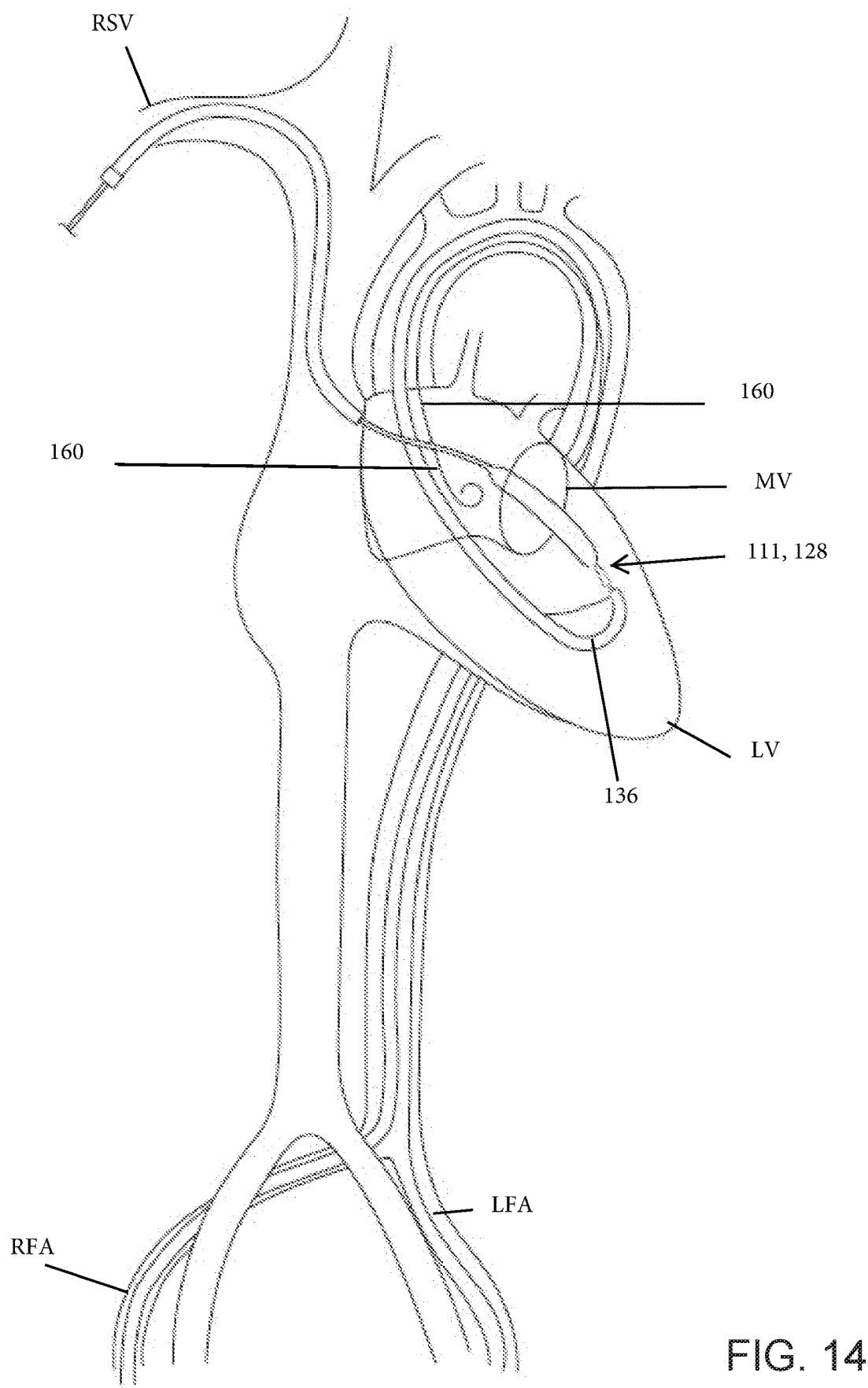
Figure 15:
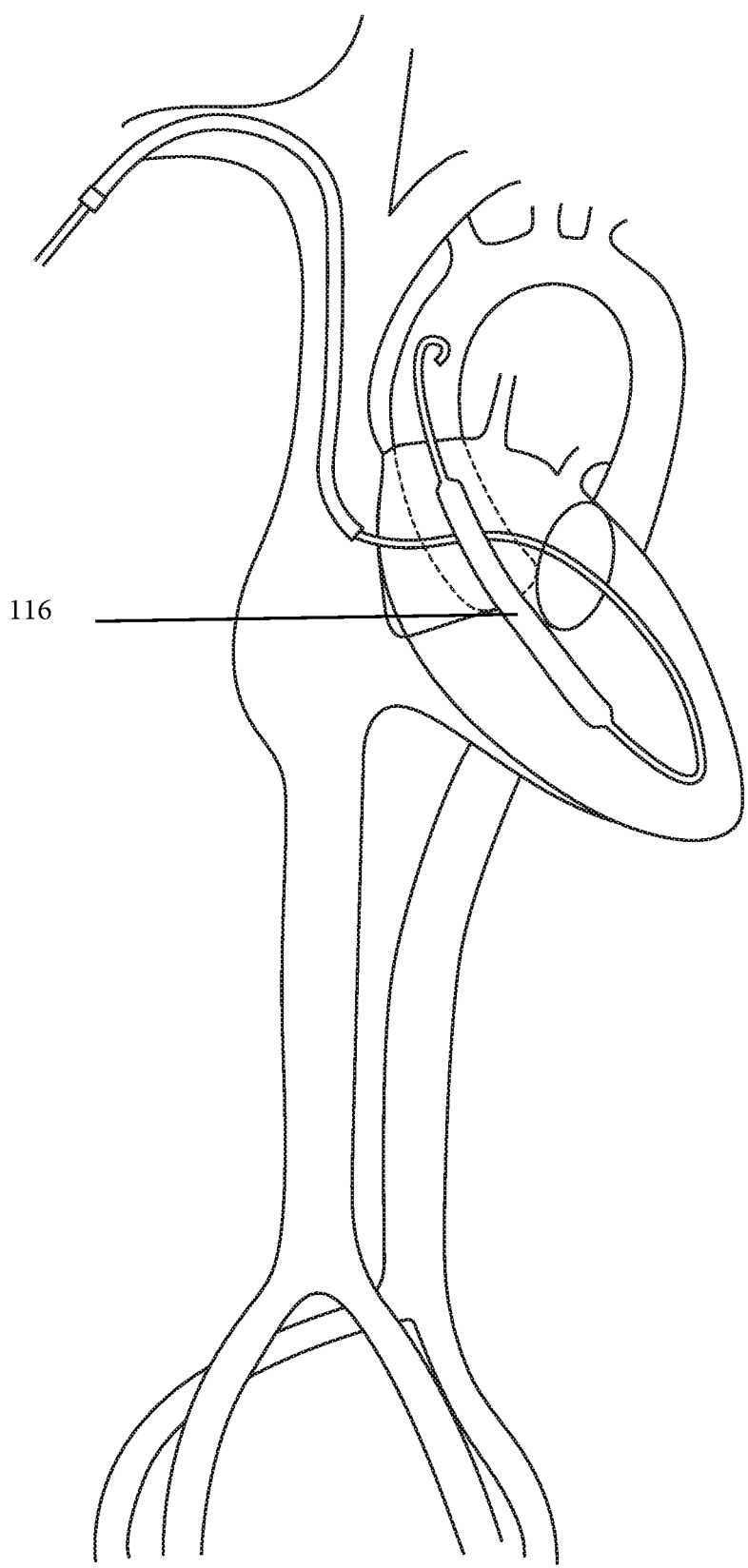

It will be seen from the discussion of FIGS. 13 and 14 below that, during delivery of the pVAD, the advancer element 120 is connected to an engagement device and pulled by the engagement device through the vasculature. The engageable feature/tip element 124 provides a secure member that the engagement device can securely engage for this important step in the process. After the pVAD is positioned in the heart and released from the engagement device, the shape memory element 122 within the advancer 120 allows the pigtail (which is pulled to a straightened shape as the pVAD is drawn through the vasculature) to return to its curled configuration. Without the shape memory element 122 the polymeric extrusion of the pigtail could deform as a result of the tensile forces occurring as it is pulled through the vasculature and thus be left with a straightened shape that could scrape the endothelial surface of the aorta at the implant site.

Engagement Devices

As discussed in connection with the engageable features/ tips 108, 110 of the cable 106 and the engageable feature/tip 124 of the pVAD, the system includes one or more engagement devices that engage with these features tips at various points during use of the system. It will be understood from the method description that in some steps, such as when ends of the cable 106 are being captured within the vasculature and then exteriorized, an engagement device may take the form of a simple snare as is discussed in connection with FIGS. 9-11. For other steps, however, engagement devices are needed that can securely couple to the engageable features/tips of the cable (which will be described with respect to FIG. 12) or the pVAD (FIGS. 13-14) so that the coupled devices can be advanced together through the heart and/or vasculature.

Figure 2C:
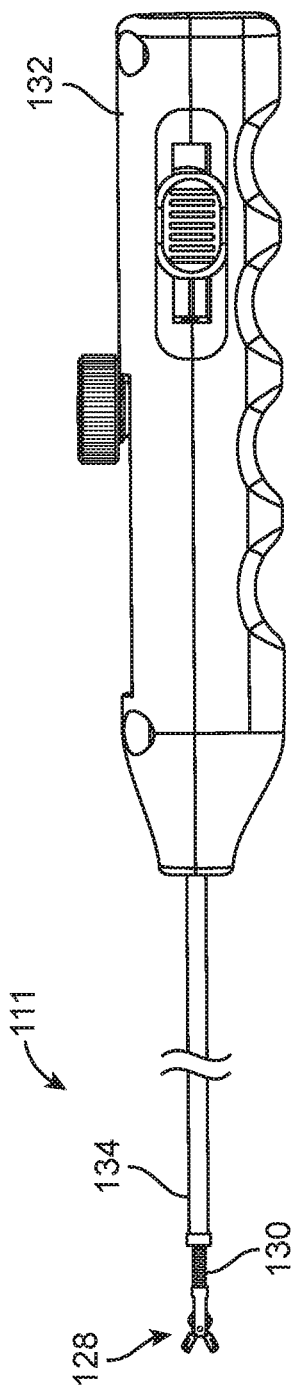
FIG. 2C is a side elevation view of a grasper.

A grasper is an example of an engagement device that will securely couple with the cable and pVAD during these steps in a manner that will hold the two devices together without risk of separation. One example of a grasper 111 is shown in FIG. 2C. Using a grasping element at its distal end, the grasper can securely and releasably engage the second engageable feature 110 of the cable 106, as well as the tip element 124 of the pVAD. The terms "grasper" and "grasping" are often associated with devices having jaw members, and FIG. 2C shows a grasper device 108 that includes jaw members, one or both of which articulates to engage the feature on the cable or pVAD that is to be engaged. However, it should be understood that the grasper can have various other suitable configurations (some which do not have jaw members), including, but not limited to, snares, internal or external collets, suture attachments, and the configurations shown and described in application Ser. No. 16/578,380, filed Sep. 22, 2019, entitled Graspers for Use in Guiding Delivery of Percutaneous Cardiac Therapeutic Devices. The terms "grasper" and "grasping device" will be used more generically in this application to describe any suitable configuration of engagement device that can be used to temporarily but securely couple with the cable or pVAD.

In the FIG. 2C embodiment, the grasper comprises jaw members 128 mounted on a flexible shaft 130. One or both of the jaw members is actuatable using actuation features on the grasper's handle 132 to move the jaws between opened and closed positions. The grasper may additionally include an outer tube 134 slidably positioned on the shaft. An additional actuator would then be included on the handle for moving the outer tube 134 between a proximal position in which it is proximally spaced from the jaws, and a distal position in which it telescopes over the closed jaws to prevent them from unintentionally opening. The handle may include lock(s) engageable to lock the jaws in the closed position and/or lock the tube in the distal position, in each case to prevent unintending release of the cable or pVAD.

FIGS. 3C-3F illustrate the steps of securely engaging the advancer 120 using the grasper 111. The advancer 120 is moved from its curled position (FIG. 3C) to a generally straightened position (FIG. 3D) and inserted between the jaws of grasper. The jaws are moved to the closed position (FIG. 3E) to capture the engageable feature/tip element 124, and then the outer tube 134 is advanced distally (FIG. 3F) to retain the jaws in the closed position.

In a modification to this embodiment, illustrated in the sequence of FIGS. 3-3J, the jaws 128a are mounted on a shaft 130a that includes a lumen. To lock the grasper to the pVAD, the advancer 120 is moved to a straightened position (FIG. 3H) and inserted between the jaws of the jaw member 128a and into the lumen of the shaft 130a (FIG. 3I). Once the advancer 120 is fully inserted into the lumen, the outer tube 134 is advanced distally (FIG. 3J) to squeeze the jaws closed. In this step engagement elements of the jaw capture the corresponding engageable feature of the advancer. As an alternative to the engagement features discussed above, the advancer shown in this embodiment includes one in the form of an annular groove at its tip. Features (e.g. detents) in the jaws engage, or seat in, the grooves as they close on the advancer. A lock positioned at the handle (not shown) of the grasper locks the outer tube in its distal position until the user is ready to release the pVAD from the grasper, at which time the user unlocks the outer tube and withdraws it from its distal position over the jaws.

Left Ventricle Redirector

Figures 4A, 4B:
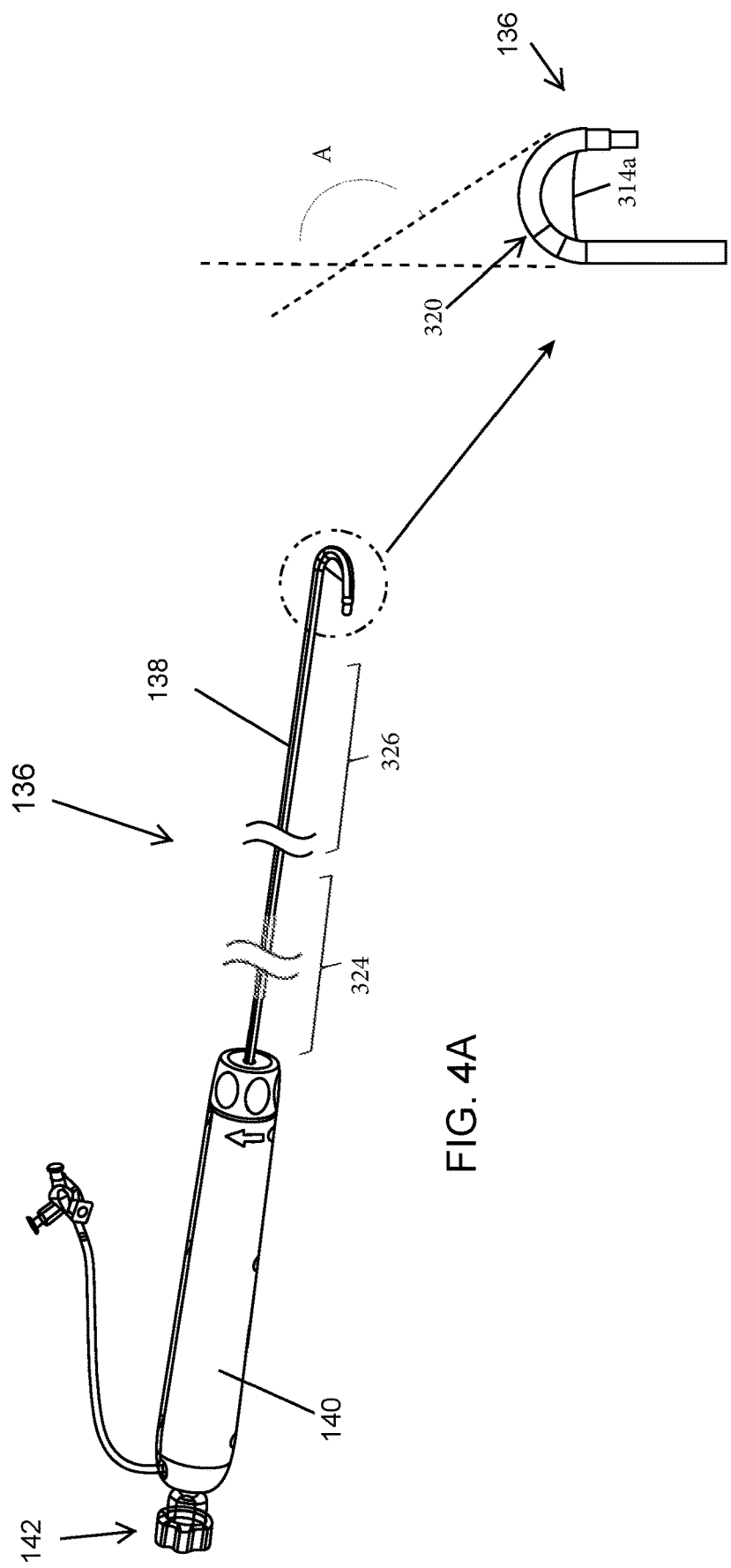
FIG. 4A is a perspective view of a left ventricle redirector ("LVR")
FIG. 4B is a side elevation view of the portion of the left ventricle redirector encircled in FIG. 4A.
Figure 4D:
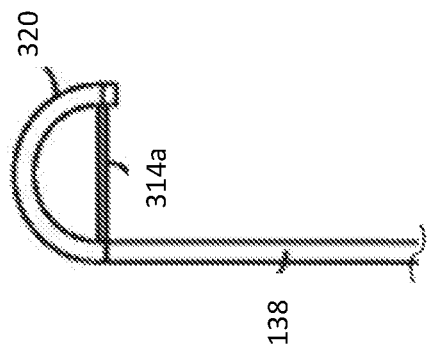
FIGS. 4C and 4D are side elevation views of alternative embodiments of distal tip sections for the LVR, each shown in the curved position.

The system further includes a left ventricle redirector or "LVR" 136, which is shown in FIGS. 4A and 4B and described in greater detail in application Ser. No. 16/578, 379, entitled Device and Instrument for Facilitating Transseptal Delivery of Cardiac Therapeutic Devices, filed Sep. 22, 2019 (SYNC-5300), which is incorporated herein by reference. The LVR includes an elongate catheter shaft 138 having a proximal handle 140 with a proximal access port 142 and a flush port. The shaft includes a lumen 308 accessible via the access port 142. This lumen extends to the distal tip of the shaft.

FIG. 4F is a cross-section view showing the shaft construction. As shown, a lubricious layer such as an extruded PTFE liner 310 lines the wall of the lumen 308, and a braid 312 covers the liner 310. Incorporated between the liner 310 and braid 312 are a pair of pullwires 314a, 314 and a return wire 316. The pull wires 314a, 314b are directly adjacent to one another. Their side-by-side positioning causes bending of the LVR along a bending plane P1 when tension on the wires is increased.

The return wire is positioned 180° from the pull wires as shown. It may have a rectangular diameter with the long edges oriented to cause the shaft to preferentially bend along bending plane P1. One of the pullwires 314a exits and then re-enters the shaft towards the shaft's distal end. This will be explained in the description of FIGS. 4B and 4C.

An outer jacket 318 of polymeric material (e.g. polyether block amide, "PEBA," such as that sold under the brand name Pebax) 314 covers the braid 312. During manufacture of the shaft, the polymeric material is positioned over the braid and subjected to a reflow process to flow the polymeric material over the braid. The material properties of the polymeric material vary along the length of the shaft. This is discussed below.

Figure 4C:
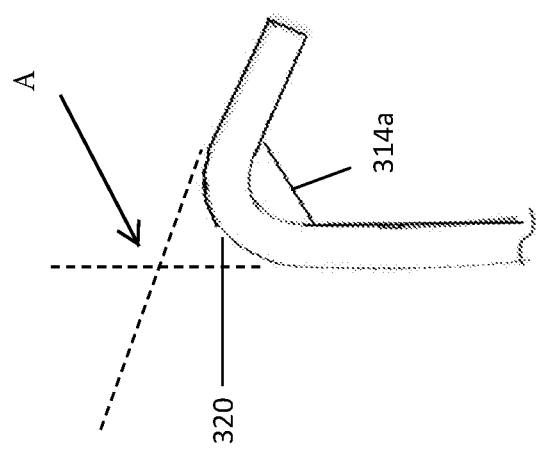

The distal end of the shaft is moveable between the generally straight position shown in FIG. 4C, and an articulated position in which the distal end is formed into a curve, as shown in FIG. 4B. The parts of the shaft that are proximal to the curve 320 may be collectively referred to as the main body of the shaft. The maximum articulation angle A is in the range of 100-140 degrees, with a more preferred range of 110-135 degrees, but may be different depending on the application for which the LVR will be used. The handle 140 (FIG. 1A) includes actuators to actuate the pull wires 314a, 314b to bend the shaft and to actuate the return wire 316 to return the distal end of the shaft to the generally straight configuration.

One of the pullwires 314a exits the sidewall of the shaft near the shaft's distal end, runs along the exterior of the shaft in a distal direction, and re-enters the shaft at the distal end of the shaft, while the other pull wire 314b does not exit the shaft at the distal end. The dual pull wire configuration advantageously allows articulation to the desired curvature and locking of the articulation in that curvature despite high loads experienced at the tip of the LVR during use.

The pull wire 314b that remains inside the shaft ("internal pull wire") helps maintain the patency of the shaft's lumen during articulation, preventing the shaft from buckling or kinking despite the large degree of articulation as would likely happen if the construction used only the external pull wire.

The pullwire 314a that exits the shaft (the "external pull wire") functions as a locking mechanism to lock the shaft in its articulated orientation, preventing the curve from opening when the outer circumference of the curve is against the left ventricular apex and forces are exerted against the distal tip of the LVR. For example, in the step discussed in connection with FIG. 14, the distal nose of the pVAD pushes against the distal tip of the LVR with great force. The external pullwire 314a maintains the curve on the LVR during this step, thus keeping the nose of the pVAD pointed downwardly so as to avoid injury to the surrounding tissue.

During use of the LVR, such forces will include forces along vectors that, without the locking provided by the external pull wire 314a, would push the distal end out of its articulated shape and towards a more straight position. The locking achieved by the pull wire 314a causes the LVR to generally retain its original shape of articulation when subjected to over approximately 40N, over approximately 50N or 60N, and even over approximately 70N along those vectors (including in an axial direction against the tip as depicted by arrow F in FIGS. 1C and 1D). The loading capability is dependent on the wire size and construction and can be tailored to suit the application for which the LVR is needed. By "generally retain its original shape of articulation" it is meant that the shape of the curve in the region bridged by the external pull wire 314a (region 332) does not significantly change. In one experiment, an LVR of wall thickness 0.026" retained its articulated shape when subjected to an axial force F of 72.5 N on the distal tip of the articulated LVR, whereas an identical LVR made of the same wall thickness but without the pull wire 314a lost its articulated shape under a force F of less than 20N. This will be discussed in more detail in connection with FIGS. 4G-4K.

Another, related, feature of the LVR is that when its tip is subjected to the forces described in the prior paragraph, the length of the pull wire 114*b* that is exposed outside the shaft 102 remains generally constant.

Note that the terms "pullwire" and "wire" are not intended to mean that the pullwires must be formed of wire, as these terms are used more broadly in this application to represent any sort of tendon, cable, or other elongate element the tension on which may be adjusted to change the shape of the LVR. Also, while the term "straight" is used to refer to the shape of the LVR distal portion in its non-articulated position, it should be pointed out that the catheter's inherent flexibility in the non-articulated position may cause it to bend under forces of gravity when held upright, or to curve when tracked over a curved cable or wire, or advanced into contact with another structure. The term "straight" thus should not be used to interpret this application or the corresponding claims as requiring that portion of the LVR shaft to hold a straight shape.

The pullwire and return wire configuration shown in FIG. 4F also provides for steering in two directions, with movement occurring along one plane P1 between straight and curved positions. Other embodiments can be configured with additional directions of movement if desired.

The shape of the curve formed on actuation of the pullwires may differ for different embodiments. In the example shown in FIGS. 4B and 4D, the shaft curves about a relatively large radius as shown to produce a fairly shallow curve. In these embodiments, the straight portion of the distal end that extends beyond the curve 320 has a longitudinal axis that is parallel to the longitudinal axis of the main body of the shaft. In another embodiment shown in FIG. 4C, the shaft curves about a relatively small radius. In this embodiment, the straight portion that extends beyond the curve has a longitudinal axis that is transverse to the longitudinal axis of the main body. In a preferred embodiment, the diameter of the curve (i.e. the length along a line extending from the inside of the curve at the distal tip to where it perpendicularly intersects the main body of the shaft) is preferably in the range of 2.5-3.5 cm.

The distance between the distal location at which the pullwire 314*a* re-enters the shaft and the distalmost end of the shaft tip may also vary between embodiments. In the FIGS. 4B and 4C embodiments, that entry site may be spaced 10 or more mm from the distalmost end of the shaft tip, whereas in the FIG. 4D embodiment, the entry site may be spaced 5 mm or less from it.

Material properties of the LVR components will next be described, although materials having different properties may be used without departing from the scope of the invention. The materials for the shaft are selected to give the LVR enough column strength to be pushed through the vasculature, torqued, and tracked over a cable or wire through the aortic arch, and articulated at the distal tip section 322 without kinking, and to allow the outer circumference of the curve formed when it is articulated to be pressed into the left ventricle away from the mitral and aortic valves as will be described in connection with FIG. 14. A wire braid 312 extends through the shaft 338 to enhance the torque ability of the LVR. A lubricious liner 310 made using PTFE, UHMWPE or like material also extends through the shaft, allowing smooth relative movement between the LVR and the wires or cables that pass through it during use. The braid and liner terminate in the distal tip section 322 as will be described with respect to FIG. 4E.

Referring to FIG. 4A, the shaft 338 is of sufficient length to extend from the right or left femoral artery, up the descending aorta around the aortic arch and through the aortic valve into the left ventricle ("LV"), so that the distal tip section 322 can be moved into its curved position and seated at the LV apex. To meet this requirement, the length of shaft extending from the handle may have a length in the range of 900-1200 mm, and more preferably in the range of 1000-1100 mm. The materials used for the outer jacket 318 of the shaft vary along the shaft's length. The shaft includes a rigid section, formed of L25 nylon or similar material, that is disposed within the handle. In the most proximal section 324 of the shaft lying outside the handle, the jacket is formed of fairly rigid polymeric of at least 72D shore hardness, to give the LVR the column strength needed for advancement through the vasculature. When the LVR is positioned with the curve in the left ventricle, this section sits within the aortic arch and externalizes through the introducer in the femoral artery. Within the handle, the jacket 318 may include both 72D PEBA and L25 Nylon, to further enhance column strength.

The next most distal section 326 uses a somewhat more flexible, but not highly flexible, material, such as 55D PEBA or similar material. Segment 326, during use, traverses the aortic arch and sits within the left ventricle.

Referring now to FIG. 4E which shows the distal tip section in its straight position. The distal tip section 322 of the preferred embodiment includes five segments. In each of these segments the outer jacket 318 has different rigidity compared with the adjacent segments. The most proximal of these segments 328 is adjacent to section 326 described in the previous paragraph. It is a short section with a jacket of a rigid material (e.g. 72D PEBA). It is through the wall of this segment that the pullwire 314*a* extends from inside the shaft to outside the shaft. The rigid material helps prevent tearing around the opening through which the pullwire passes 314*a* even when the pullwire is highly tensioned.

In the distally adjacent segment 130, a slightly less rigid material is used (e.g. 55D PEBA). This is done to provide a gradual transition between the rigid segment 328 and the next adjacent segment 332 which is highly flexible. The transition segment helps to avoid buckling.

Segment 332 is the longest segment within the distal tip section 322 and it is designed to facilitate bending of the shaft into the curve during articulation using the pullwires. It has a jacket made from a very flexible material (e.g. 35D PEBA). The braid 312 (not shown in FIG. 4E) terminates at the distal end of this segment 332. The external pull wire 314*a* extends along the exterior surface of section 322 as shown in FIG. 4E.

Distally adjacent to flexible segment 332 is the segment 334 in which the pullwire 314*a* re-enters the shaft, and it is also the segment in which the pullwires 314*a*, 314*b* and return wire 316 are anchored to a pull ring (visible in dashed lines in FIG. 2). It is formed of a rigid material (e.g. 72D PEBA). The lubricious liner 310 may terminate at the distal end of segment 334.

The distal most segment 336 provides an atraumatic tip for the shaft. Also, during use of the LVR in the manner described below, another device is inserted into, pressed axially against, or received by its distal tip as it is held securely in the left ventricle or disposed in the vasculature. The segment 336 must have sufficient wall thickness so that it will not collapse or tear when the other device (e.g. the RLC as discussed in connection with FIG. 11, or the advancer that is engaged by the grasper as discussed in connection with FIG. 14, or the distal nose of the pVAD, as also described in connection with FIG. 14) is inserted into it or pressed against it. It is formed of highly flexible polymeric material, such as 35D PEBA having a sufficiently thick wall thickness and luminal diameter to be able to receive the device without collapsing.

In one embodiment, the polymeric material of the distal segment 334 is doped with BaSO4 to allow the tip of the LVR to be seen on the fluoroscopic image. Alternatively, a marker band made from radiopaque material may be positioned near the tip.

The flexural properties, and thus the stiffness, of the LVR are sensitive to the durometer of the extrusions forming the shaft, the reinforcement configurations used in the shaft (e.g. the braid and optional reinforcing wire, if used) and the geometry of the shaft. In a preferred embodiment made with the materials described above, an inner diameter of approximately 10.3 Fr and an outer diameter of 14.5-15.3 Fr, the region rigidity of the shaft increases by a factor of approximately two as it transitions from region 326 proximally to the region that is disposed within the handle, giving the LVR column strength that will allow it to be pushed against the LV apex when pushed from the femoral artery as described in connection with FIG. 14.

A discussion of the actuation mechanism for the pull wires 314a, 314b and return wire 316 will next be described. In general, the handle 140 is configured to move the pull wires 314a, 314b in a first direction (preferably proximally) while simultaneously moving the return wire 316 in a second, opposite direction (preferably distally), in order to articulate the LVR to the curved position. Reversing the respective directions of motion of the pull wires 314a, 314b and return wire 316 moves the LVR back to the generally straight position.

Figure 4G:
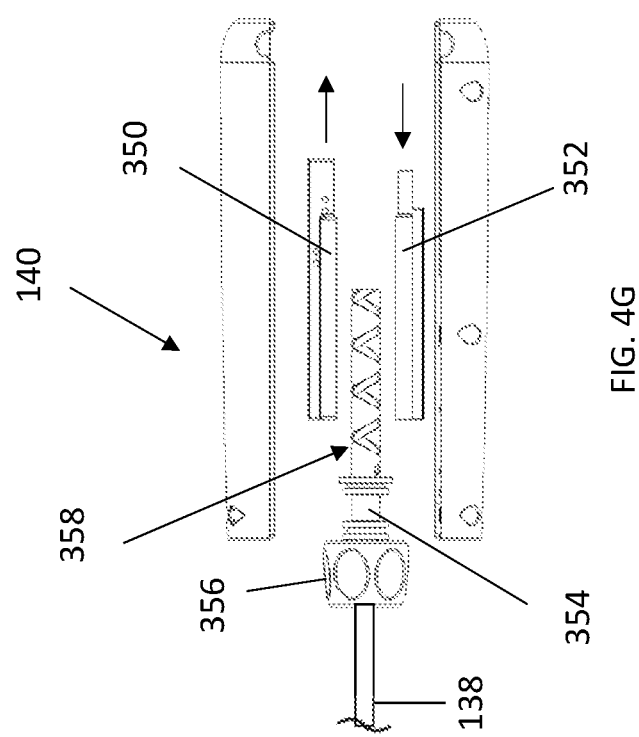
FIG. 4G is an exploded view of the handle of the LVR shown in FIG. 4A.

Referring to FIG. 4G, within the handle 140 are a first sliding member 350 and a second sliding member 352, each of which is moveable longitudinally within the handle. For convenience the term "slider" will be used as shorthand for "sliding member."

The handle 140 includes a mechanism for simultaneously moving the sliders 350, 352 in opposite directions. Various mechanisms can be used for this purpose. One exemplary mechanism, shown in FIG. 4G, includes a barrel 354 that axially rotates relative to the handle 140 when the user rotates actuation knob 356. Helical features 358 on the barrel 354 are operatively associated with helical features (not visible in the drawings) in each slider 350, 352, with the helical features 358 that interact with slider 350 being of opposite hand to those that interact with slider 352. Thus, rotation of the knob 356 in a first direction causes slider 350 to move proximally while slider 352 moves distally (see arrows in FIG. 4G), and rotation of the knob 356 in the opposite direction causes slider 350 to move distally while slider 352 moves proximally. The pull wires 314a, 314b (not shown in FIG. 4G) extend into the handle 140 from the LVR shaft 138 and are actuatable by first slider 350, while the return wire 316, which also extends into the handle from the LVR shaft, is actuatable by the second slider 352. With this configuration, motion of the sliders 350, 352 causes both pull wires 314a, 314b to be pulled as the return wire 316 is simultaneously pushed, and vice versa. Note that while the knob 356 and barrel 358 assembly is a convenient way to actuate this motion using a single input from the user, alternative mechanisms can be used without departing from the scope of the claims.

The two pull wires 314a, 314b must travel different distances during articulation, due to the fact that the internal pull wire 314b traverses the curve resulting from the articulation from its position within the shaft, while the external pull wire 314a traverses a shorter path between the point at which it exits the shaft and the point at which it re-enters the shaft. The wires must therefore be actuated at different positions within the handle so as to ensure that the external pull wire 314a maintains equal or greater tension than the internal pull wire 314b. This avoids wire slack and ensures that the locking mechanism does not relax during application of forces F at the LVR's tip.

FIGS. 4H-4J are a sequence of drawings illustrate a configuration for the slider 350 that is designed to actuate the pull wires 314a, 314b from different positions. Each pull wire 314a, 314b is shown with an actuation feature 315a, 315b at its proximal end. The actuation feature can be any feature that will be engaged by a corresponding feature of the slider 350 as the slider moves into contact with the actuation feature. In this embodiment the actuations feature 315a, 315b are elements, on the proximal ends of the pull wires, that have diameters wider than the diameter of the pull wire itself. In this particular example, the actuation feature for each wire is its corresponding crimp.

Distal to each actuation feature 315a, 315b is a corresponding feature of the slider that will engage that actuation feature as the slider 350 moves in the proximal direction (indicated by the arrow in FIG. 4H). In the embodiment depicted in the drawings, the pull wires 314a, 314b have their proximal ends positioned proximal to a proximally facing face 360. The pull wires 314a, 314b may extend through openings in the member on which the face is position as illustrated in FIG. 4K. Each opening is smaller in diameter than the diameter of the actuation feature 315a, 315b. The face 360 serves to engage the actuation feature 315a, 315b of each pull wire 314a, 314b as the slider 350 moves proximally. Note that there may be two separate members having faces 360a, 360b (see FIG. 4L), one for each of the pull wires 314a, 314b, or the face 360 may be divided by a longitudinal barrier 362 that maintains separation between the proximal ends of each pull wire as shown in FIGS. 4H-4J.

FIG. 4H depicts the slider 350 and pull wires 314a, 314b when the LVR is in the generally straight (non-articulated) position. As shown, the length of the external pull wire 314a is shorter than that of the internal pull wire 314b, so that when the slider 3150 moves proximally, the external pull wire 314a is actuated by engagement feature/surface 360 first (FIG. 4I), and it is then pulled a predetermined distance before the internal pull wire 314b is actuated by engagement feature 360 (see FIG. 4J, which shows the pull wires after actuation of the internal pull wire 314b has begun). This ensures that the loading of the external pull wire is higher than, or at least equal to, the external pull wire, as discussed above. From the position shown in FIG. 4J, proximal movement of the slider continues until the pull wires 314a, 314b bring the shaft to its fully articulated position.

In an alternative arrangement shown in FIG. 4L, the slider may have separate features 360a, 360b positioned to actuate the pull wires 314a, 314b at different points along the slider's travel. FIG. 4L depicts these features of the slider and the pull wires when the LVR is in the generally straight (non-articulated) position. The features 360a,360b are positioned on slider so that as slider moves proximally, feature 360a engages external pull wire 314a (e.g. at crimp 315b or other actuation feature as discussed above) and pulls it a predetermined distance before the feature 360b similarly actuates internal pull wire 314b.

In each of the above actuation embodiments, the distance by which external pull wire 314a will travel before internal pull wire 314b is engaged is selected to be the approximate difference between L1 and L2. In this calculation, L1 is the length of external pull wire 314a between its exit and entry points into and out of the shaft when the LVR is in the fully articulated position. L2 is the length traversed by the internal pull wire 314b along the internal circumference of the curve, measured between the points on the internal pull wire's path that are circumferentially adjacent to the points at which the adjacent external pull wire exits and then re-enters the shaft.

In some embodiments, an electronic drive unit may be used to deliver precisely coordinated pushing and pulling forces. An example of this type of drive unit is given in WO/2018/098210.

Tracker Balloon Catheter

Figure 8:
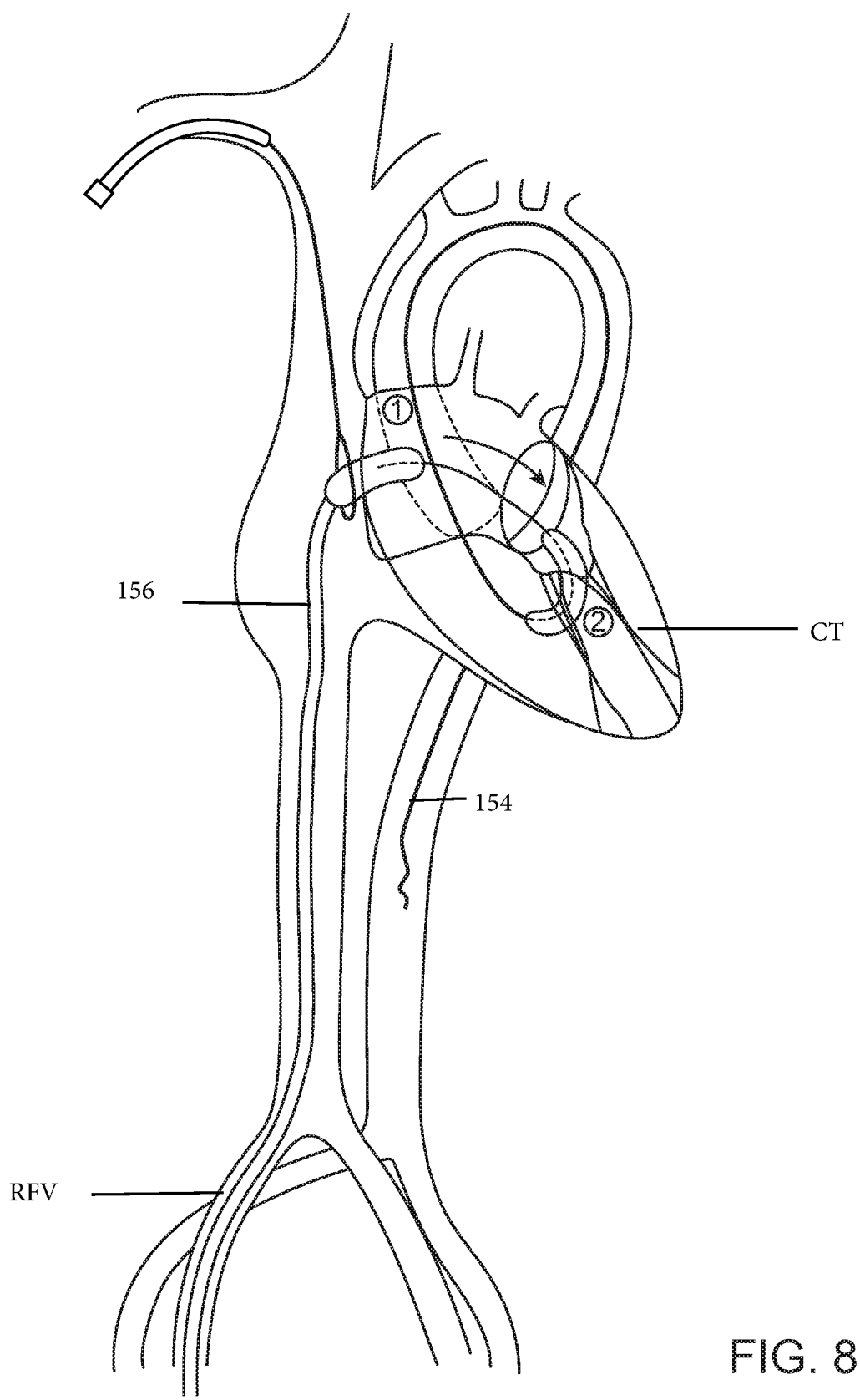

FIGS. 5A-5C show a tracker balloon catheter 400 that may be optionally part of the system and may be constructed in different lengths and made of different materials depending on the particular application. In one embodiment in may be used to float from the interatrial septum to the distal aorta and would have the short length illustrated in FIGS. 5 and 16B. This balloon shown in this embodiment would be made using an elastomer such as latex. An alternative embodiment would be longer and made from a non-elastic polymer such as PTFE, as described below in FIG. 8, for atrial septostomy and to assess whether the wire is free of involvement of the chordae tendinae of the mitral valve. The balloon catheter 400 has an elongate shaft and a balloon 402 at the distal end of the shaft. The balloon 402 is inflatable using a fluid medium such as saline introduced through the proximal port of the catheter.

The balloon is uniquely shaped for its use in the method disclosed herein. In particular, unlike a conventional balloon dilation catheter which has a tapered distal nose, the balloon 402 has an approximately cylindrical shape with a distal face 404, which, in one embodiment, may be generally flat. Unlike traditional balloon catheters in which the catheter tip is positioned distal to the distalmost part of the balloon, in the balloon 402 the tip of the catheter shaft preferably does not extend beyond the distalmost part of the balloon. In the steps described with respect to the embodiment shown in FIG. 8 below, this shape prevents the balloon from slipping between chordae in the event the wire it tracks over is running between the chordae. Instead, the user would feel the balloon come to a stop against the chordae and would thus recognize that repositioning of the wire is needed.

The balloon 400 may also have a concave proximal face, or a concave region or invagination 406 in the proximal face. This may be in the region surrounding the connection to the shaft as shown in FIG. 5C. The concavity in the proximal face increases the surface area of the balloon in the upstream direction and consequently facilitates movement of the balloon in the downstream direction during use.

First Embodiment—Method of Use

A method of using the system to deliver a pVAD to its operative location within the heart will next be described with reference to FIGS. 6A-15.

Figure 6A:
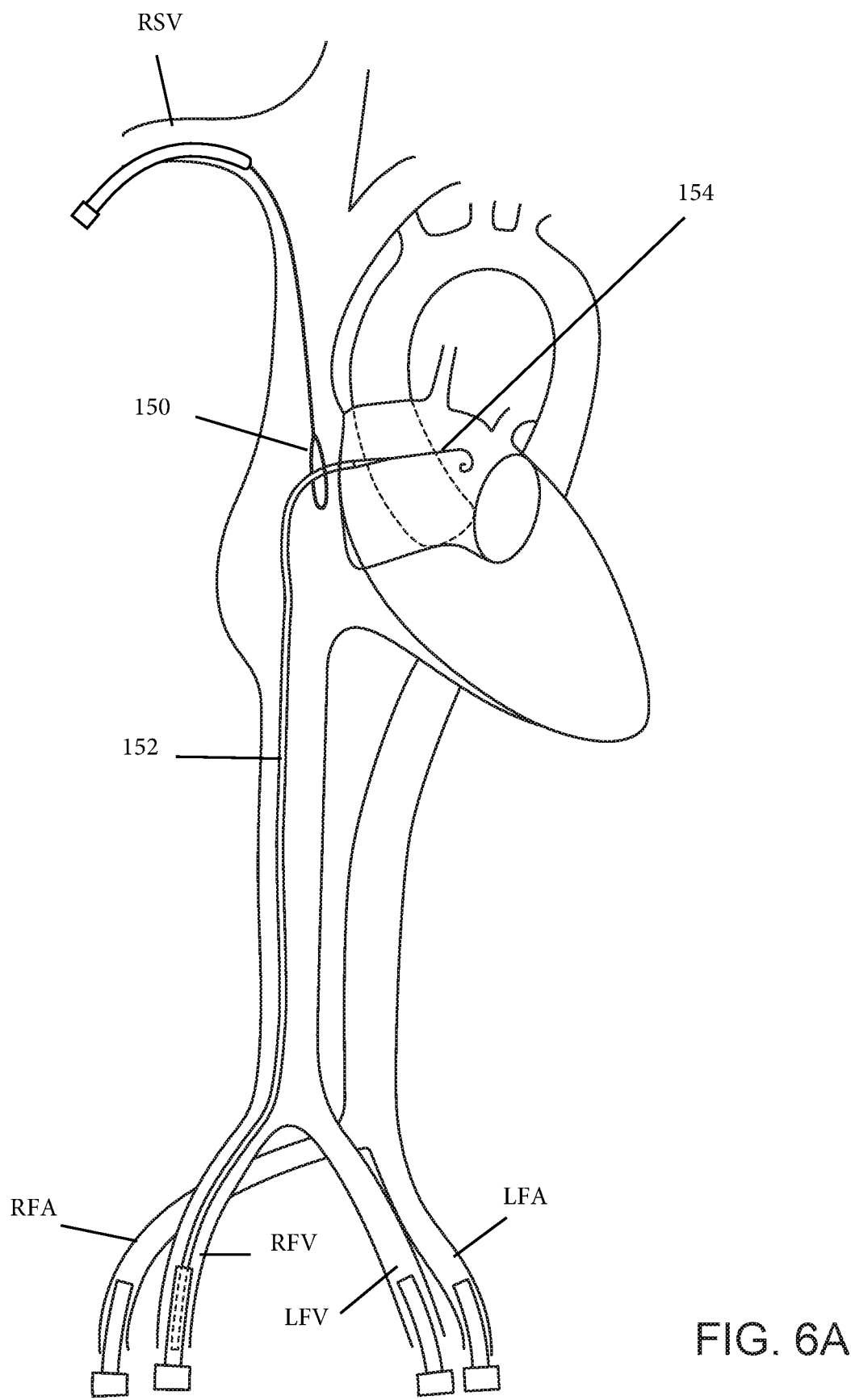
Figure 6B:
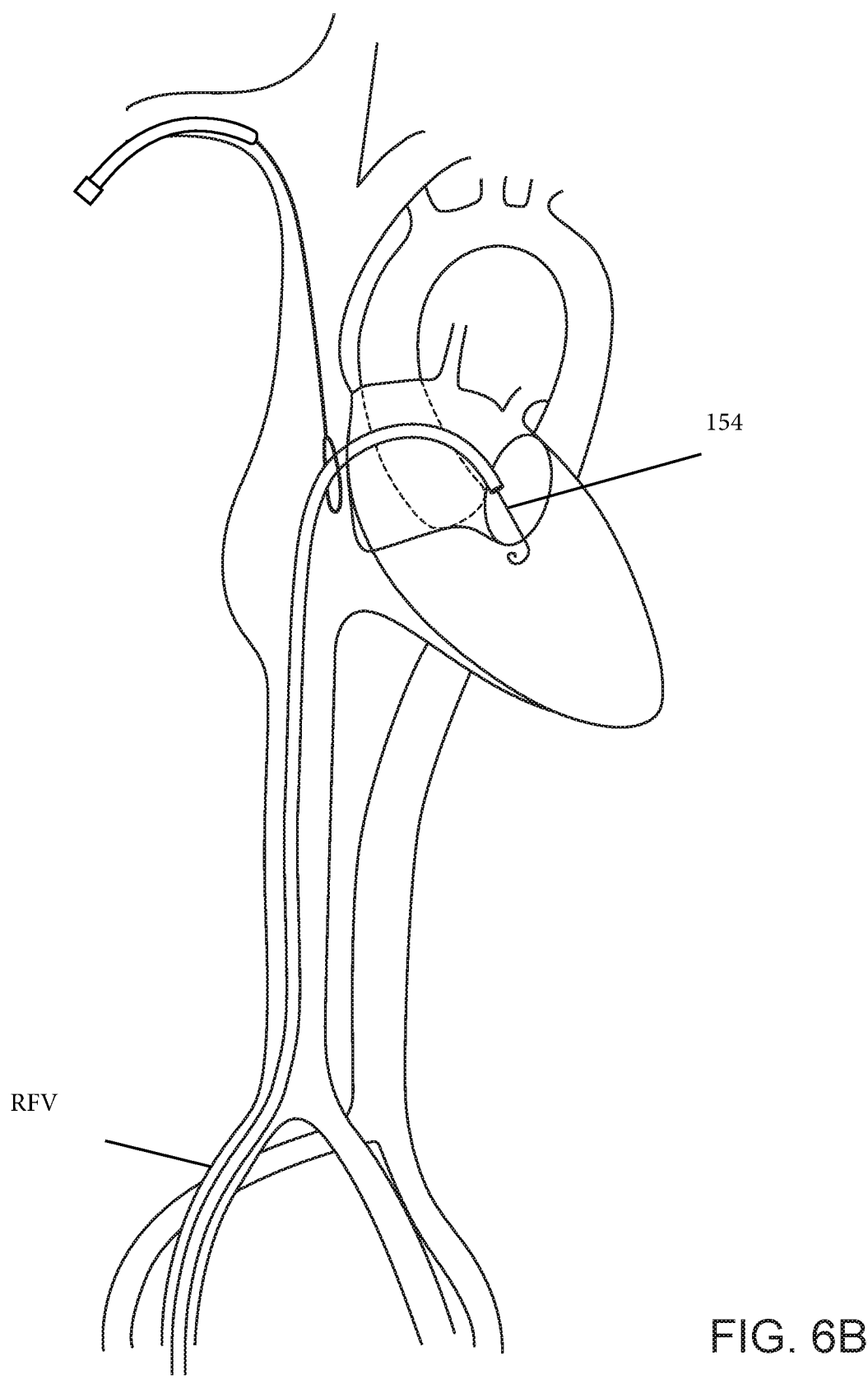

As an initial step, the practitioner obtains percutaneous access to the vessels that will be used in the procedure using percutaneous access sheaths. This will include the right femoral artery (RFA) and or the left femoral artery (LFA), the right femoral vein (RFV-11 F sheath) and/or the left femoral vein (LFV-11 F sheath), and the right subclavian vein (RSV) or another site for superior access. Examples of alternative superior access points include the left subclavian vein, or the right or left internal jugular vein. FIG. 6A shows percutaneous access sheaths positioned in each of these vessels. Access sheath sizes are selected in sizes suitable for the devices that are to be passed through them.

A snare 150 is inserted through the RSV into the right atrium as shown in FIG. 6A. The loop of the snare is placed, in its open position, adjacent to the interatrial septum.

A Brockenbrough transseptal catheter (BTC) 152 is introduced through the RFV and, using the well-known technique of transseptal catheterization, is passed from the right atrium (RA) into the left atrium (LA). The right and left atrium are not labeled in FIG. 6A. It is beneficial to pass the BTC through the loop of the snare 150 for reasons that will become apparent. A wire 154, which may be an 0.035" wire such as the Abbott Versacore wire, is passed through the BTC and into the left atrium (LA).

Figure 7:
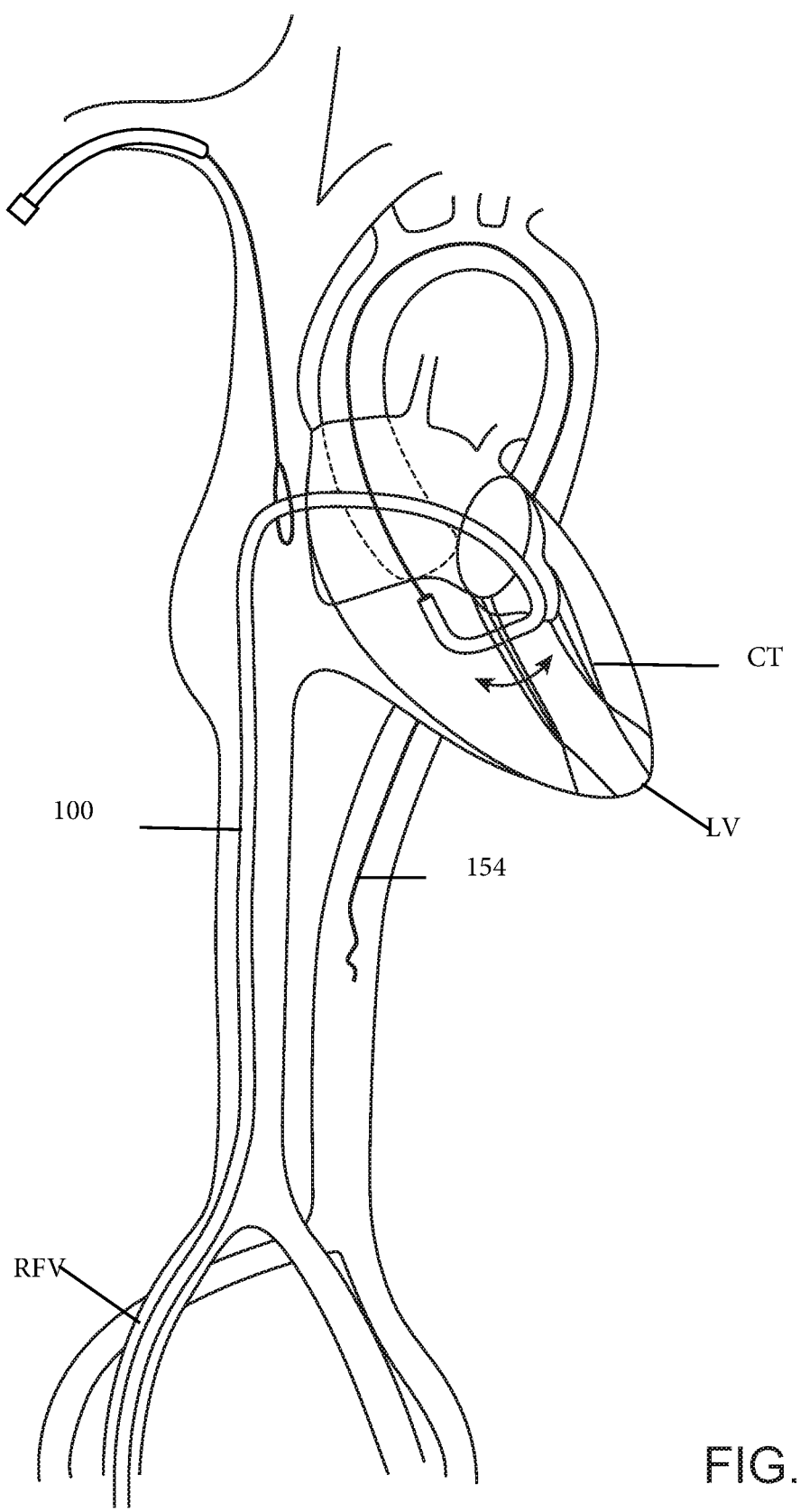

The BTC 152 is withdrawn at the RFV and exchanged for an RLC 100 which is advanced over the wire. See FIG. 6B. The RLC which preferably has been filled with an 80/20 saline-contrast solution for additional visibility under fluoroscopy. After it has crossed the inter-atrial septum into the LA, the RLC 100 is advanced toward the lateral edge of the LA, and the wire 154 is pulled back into the RLC, proximal to the loop (see FIG. 1) of the RLC. The RLC is rotated counterclockwise about the axis of the main body of its shaft as the RLC is slowly withdrawn. This motion causes the tip of the RLC to drop in an inferior direction into and through the mitral valve MV towards the left ventricle. Once the tip is through the MV, the RLC continues to be advanced, its shape causing the distal end of the tip to move in a right-ward (the patient's right) and anterior direction. Some rotation of the RLC may be needed in this step to get the tip towards the AV. This direction of motion is needed to orient the RLC's tip towards the aortic valve, since the aortic valve is anterior and to the right of the mitral valve FIG. 7 shows the distal tip of the RLC pointed towards the aortic valve. As shown, section 104 of the RLC extends within the inferior vena cava (not shown), extends through the inter-atrial septum S, drops into the mitral valve and forward into the left ventricle. Note with regard to this drawing that the distal curve 212 is positioned anterior (out of the plane of the drawing towards the viewer) with respect to the proximal curve.

The practitioner may, at this point, wish to verify that the RLC tip is not trapped by the chordae tendineae CT of the mitral valve. This may be done by observing the fluoroscopic image and confirming the presence of a "windshield wiper" movement of the RLC tip, as such movement suggests that the tip is not entangled in the chordae. The arrows in FIG. 7 represent the "windshield wiper" motion of the distal tip of the RLC. Although the wire is shown in this drawing, the step of observing this motion of the distal tip is ideally performed before the wire is re-extended from the RLC.

When the distal portion of the RLC is positioned in the LV, its curvature directs its tip towards the aortic valve. With the RCL positioned in this way, the guide wire 154 is advanced through the aortic valve, around the aortic arch, and well down into the descending aorta, as shown in FIG. 7.

Movement of the RLC through the heart as described above is optimally performed using a variable stiffness guidewire, allowing the variations in curvature and stiffness along the length of the RLC to work together with the different degrees of regional stiffness of the guidewire. A suitable variable stiffness guidewire is one having at least three segments of different flexibility. The first, and most distal of those segments has the greatest flexibility. A second segment is proximal to the distal segment and has less flexibility than the first segment, and a third segment is proximal to, and less flexible than, the second segment. In one specific example, the first and third segments are directly adjacent to the second segment.

Where a variable stiffness guidewire is used, during the step of crossing the septum with the RCL, the stiffest segment of the guidewire is positioned through curves 212, 214 of the RLC, forming it into a gently curved configuration. In this more straightened configuration, advancement of the RLC, after it crosses the septum, causes its tip to cross the left atrium to a position beyond the mitral valve, and optionally in a left pulmonary vein. After the RLC reaches this position, the guidewire is withdrawn so the most flexible distal section, at least within the curve 212 of the RLC, causing the RLC to return to a more curved orientation due to the withdrawal of the stiff part of the guidewire from the loop 210 of the RLC. Counterclockwise torque is then applied as the RLC is withdrawn, causing the RLC tip to move anteriorly through the mitral valve. The tip will drop from the mitral valve into the left ventricle. The RLC is pushed with clockwise torque, or with alternating clockwise and counterclockwise torque, to direct the RLC tip adjacent to the ventricular septum and pointing to the left ventricular outflow tract. Next, the guidewire is advanced through the aortic valve and around the aortic arch, allowing the RLC to be advanced on the stiffer segment of the guidewire.

The RLC 100 is removed, leaving the wire 154 in place. A balloon dilation catheter 156 is advanced over the wire 154 to dilate the interatrial septum (atrial septostomy)—see balloon position (1) in FIG. 8. The balloon dilation catheter may be a traditional balloon dilation catheter such as the 12×40 mm Boston Scientific charger balloon dilation catheter, or it may be the tracker balloon catheter 400 described with respect to FIGS. 5A-5C, using the elongated non-elastic embodiment described above. Following this, as a second step, the balloon is partially deflated and advanced further over the wire and through the mitral valve orifice. The balloon is then fully inflated and advanced through the mitral valve chordae apparatus—see balloon position (2) in FIG. 8—to the aortic valve to further confirm that the wire path is not entrapped within the chordae tendinae (CT).

The balloon catheter is removed and replaced over the wire 154 with the RLC, which is now introduced at the RFV and then advanced all the way to the descending aorta. The long femoral venous sheath (not shown) is advanced up to the inter-atrial septum from the RFV to provide support for the RLC.

A second snare 158 is inserted in the RFA and advanced upward in the aorta and over the RLC 100. See FIG. 9.

With the second snare 158 secured on the RLC 100, the wire 154 is withdrawn from RLC at the RFV and exchanged for the cable 106. The cable is inserted into to RLC at the RFV with the first engageable feature 108 first.

When the cable 106 emerges from the RLC 100 in the descending aorta (DA), the second snare 158 is pulled off the end of the RLC and onto the cable. The second snare 158 is tightened around the cable 106, capturing it at the tip feature 108, and the snare is then withdrawn from the RFA to draw the end of the cable out of the body at the RFA. See FIG. 10.

Figure 11:
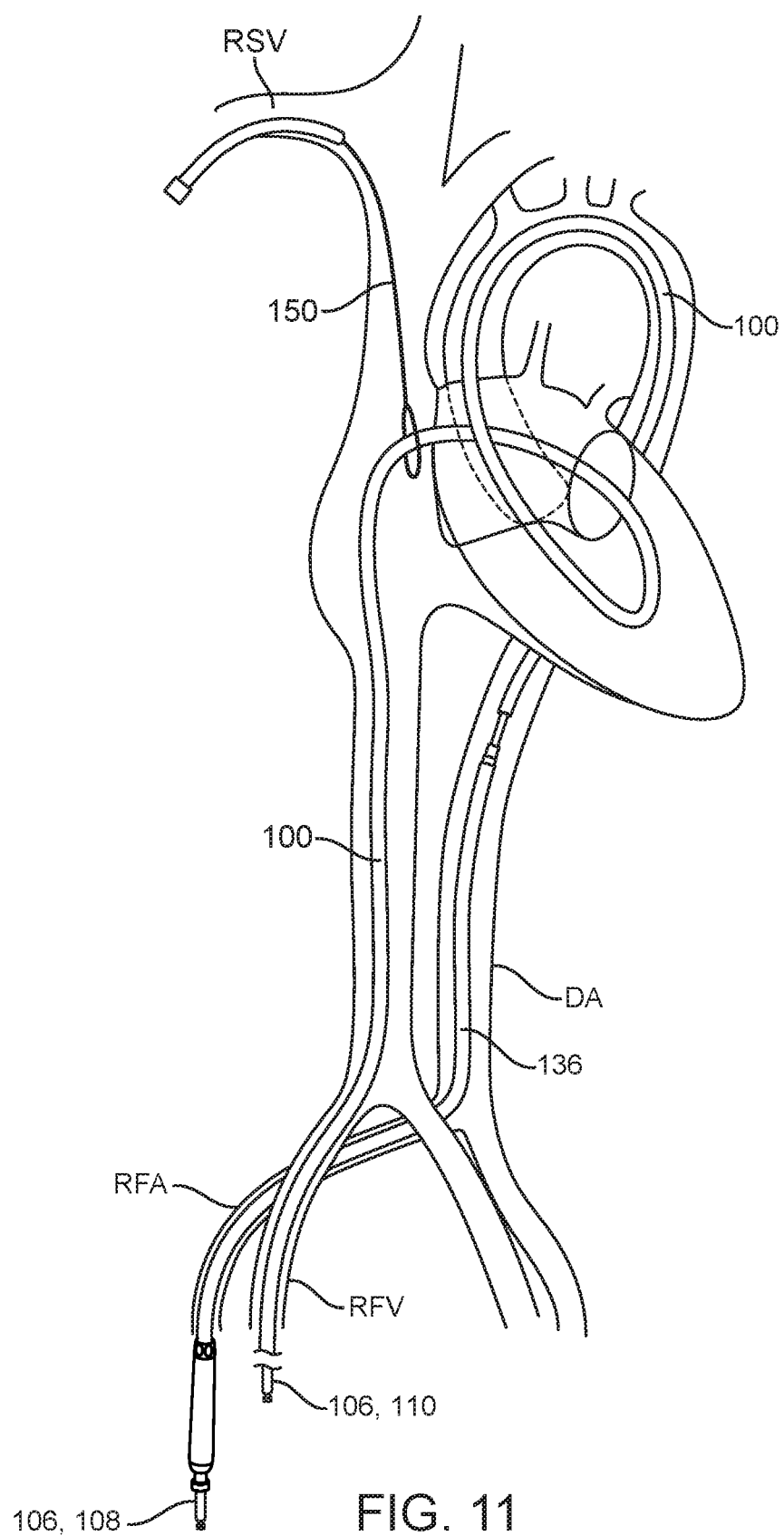

The portion of the cable 106 exteriorized at the RFA is backloaded through the LVR 136 on the operating table so that engageable tip feature 108 of the cable extends from the proximal handle of the LVR 136 as shown in FIG. 11. The LVR is advanced through the RFA sheath and advanced in the descending aorta until it touches the tip of the RLC 100. Then both the RLC and the LVR are moved together, with the LVR being advanced as the RLC is being retracted at the same rate so as to keep the ends of the LVR and RLC in contact with one another. This action moves the distal end of the LVR around the aortic arch and into its destination in the left ventricle (LV). Maintaining contact between the tips of the LVR and RLC prevents the edges around the open lumen of the LVR from causing embolization of material from the roof of the aortic arch and avoids vascular damage or damage to the aortic valve. The LVR is periodically flushed during this motion, and once positioned it may be fluidly coupled to a pressured heparinized saline source for continuous low volume flushing. This avoids the potential for thrombosis.

The RLC is then removed via the RFV sheath. The cable 106 is pulled from the RFA sheath until the opposite end of the cable 106, which is in the venous side of the vasculature, the end having the tip feature 110) is withdrawn completely into and through the RFV sheath into the inferior vena cava (IVC) above the renal veins. Next, the first snare loop 150 placed earlier via the RSV is tightened adjacent to the interatrial septum to capture the venous end (on which the tip feature 110 is located) of the cable 106 and to exteriorize it upward through the RSV sheath. See FIG. 12. As described above, the LVR is positioned in the LV at this point, but its pull wires have not yet been fully activated to lock it in its most articulated position.

Note that in modified embodiments, a superior access point other than the RSV may be used for the snare loop 150 and, subsequently, exteriorization of the cable 106. Examples of alternative superior access points include the left subclavian vein, or the right or left internal jugular vein.

Figure 12:
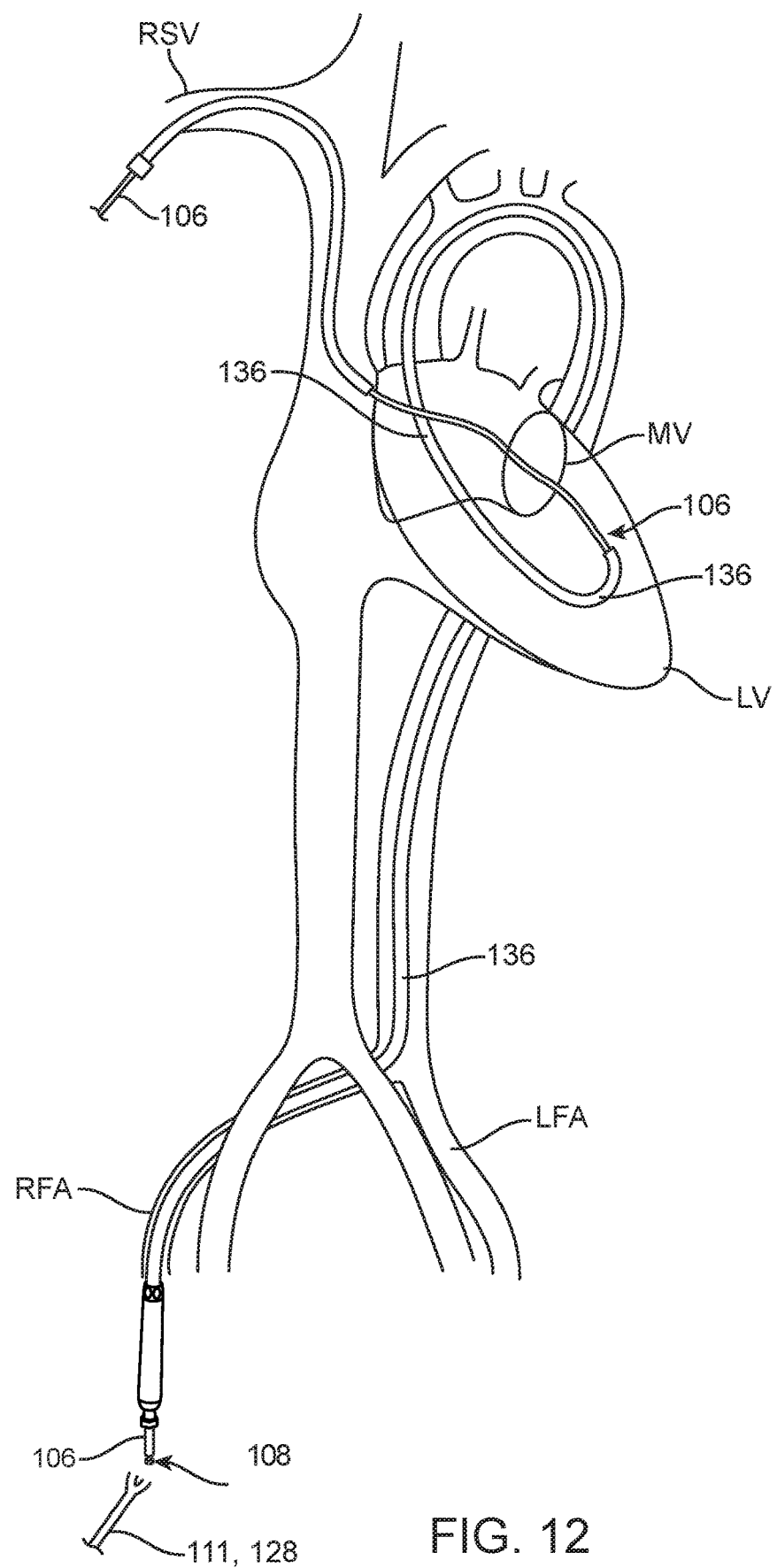

Sill referencing FIG. 12, the grasping element 128 of the grasper 111 is attached to the second engageable tip feature 108, which is on the arterial side of the cable 106, extending out the back (proximal) end of the LVR handle. The grasping element 128 is then inserted into the proximal end of the LVR, and traction is applied to the cable 106 from the RSV to advance the assembled cable 106 and grasper 111 through the LVR, which remains with its distal end positioned in the LV. This step continues until the grasping element 128 has been exteriorized from the RSV sheath.

Next, the pVAD 116 or other device that is to be delivered to the heart is engaged by the grasping element 128 of the grasper 111 that is protruding from the RSV sheath. For a pVAD having an advancer 120 with an engageable tip 124, the grasping element 128 is secured on the tip.

If not already activated, the pullwires of the LVR 136 are activated to fully form and lock the distal end of the LVR into the curved position. The LVR remains in the LV, with the curve positioned in the apex and the distal opening orientated towards the mitral valve MV. This position is shown in FIG. 14.

A pigtail catheter 160 is advanced from the LFA to the aortic valve to allow the valve position to be confirmed on the fluoroscopic image.

The pVAD 116 is advanced through the RSV sheath, which has been under continuous heparinized saline flush) as the grasper 111 (which extends from the proximal end of the LVR) is simultaneously pulled from the RFA. The distal end of the RSV sheath is advanced distally to the position shown in FIG. 14 to position its distal end close to the septum. This helps to provide support for the pVAD insertion towards the right atrium. The pVAD is advanced across the septum, LA, and LV slowly and continuously with equal pulling (of the grasper from the RFA) and pushing (of the pVAD from the RSV) forces. Before the pVAD reaches the LVR, there is an exposed length of the shaft of the grasper 111 extending from the tip of the LVR, through the mitral valve, to where the distal end of the grasper 111 is engaged to the advancer of the pVAD. Pushing the shaft of LVR from the femoral artery as the pVAD is advanced pushes the LVR's curve against the LV apex and thus keeps the exposed portion of the grasper 111 from damaging the mitral valve leaflets.

The closed grasper tip 128 and then the pVAD tip 120, 124 enter the distal luminal opening of the LVR 136 in the LV apex. The LVR and grasper are then pulled together from the RFA as the pVAD is advanced in unison toward the aortic valve. During this latter step, the curve on the LVR is straightened as it is retracted into the LV outflow tract.

The pVAD 116 is moved in this manner to its final position in the LV and across the aortic valve such that its inlet is resting away from the mitral valve and toward the ventricular apex in the LV and its outlet is positioned in the ascending aorta. Upon completion of any necessary testing for position or pump function, the pVAD is released from the grasper 111, and the LVR 136 and grasper 111 are removed under fluoroscopy from the RFA.

In the rare event that the pVAD is found to fail any functional testing, prior to release from the grasper 111, it can simply be extracted retrograde through the RSV sheath. This has the advantage of delivering the grasper 111 apparatus back through the RSV to be reintroduced after the pVAD is inspected or to reinsert a new pVAD. If at any time after insertion, it becomes desirable to remove the pVAD, it can again, simply be extracted without attachment to the grasper through the RSV. Alternatively, the pigtail can be snared and secured in the aorta, and the connector cable to the pVAD can be cut on the venous side of the interatrial septum, allowing the pVAD to be extracted anterograde from the arterial side. This may be performed using a cutting or cutting and extraction tool introduced via the internal jugular vein and advanced to the septum where it can be used to cut the connector cable to the pVAD. After cutting, the snare catheter extracts the pVAD via the aorta, and the pVAD cable is withdrawn through the internal jugular vein.

Second Embodiment

A second embodiment is similar to the system and method of the first embodiment but differs in the manner in which the conveyor cable 106 is placed.

Figure 16A:
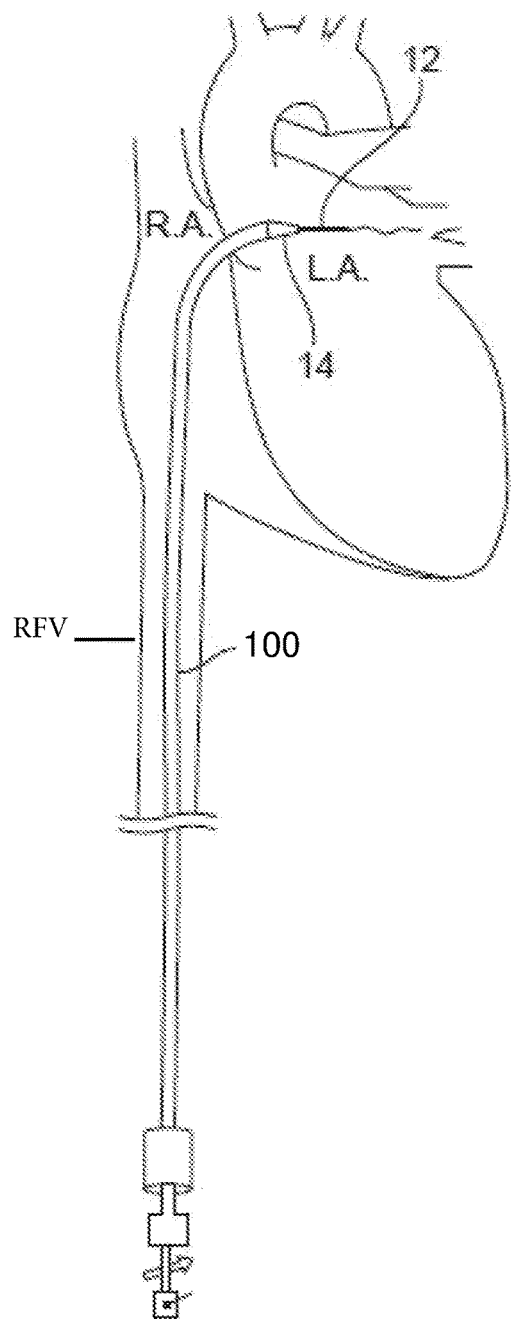
FIG. 16A schematically illustrates a section of the heart and shows an initial step of the second embodiment, in which transseptal catheterization is carried from the right atrium into the left atrium, using a Brockenbrough needle assembly through the RLC.
Figure 16B:
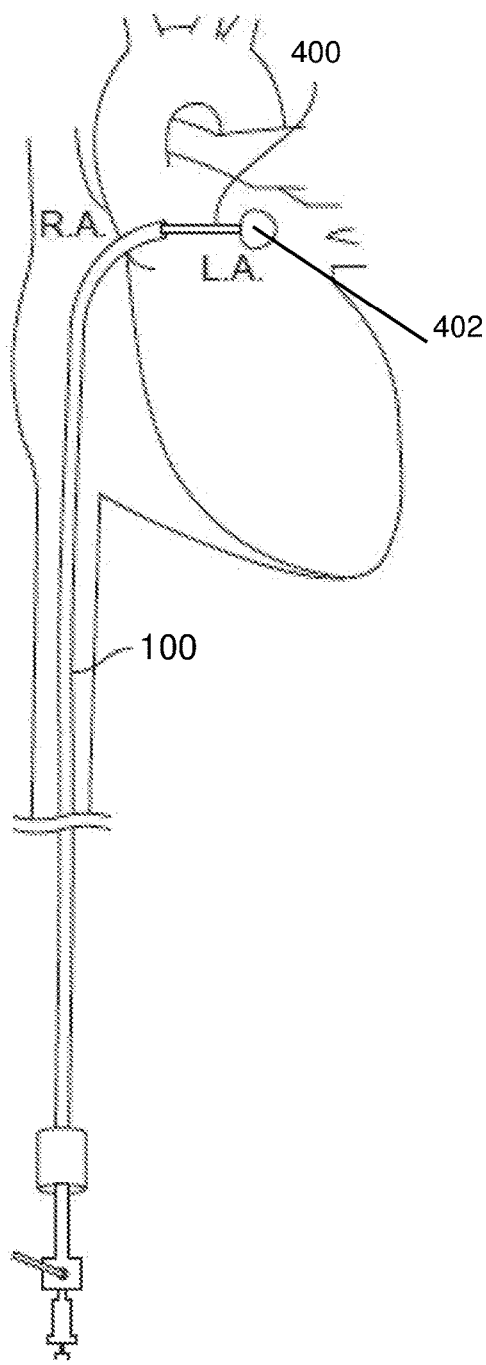
FIG. 16B is a similar view to FIG. 16A and shows the balloon catheter deployed within the left atrium.

As an initial step depicted in FIG. 16A, the RLC 100 is introduced using the well-known technique of transseptal catheterization from the right atrium (RA) into the left atrium (LA), such as by using a Brockenbrough needle assembly 12, 14 through the RLC 100, which is positioned in the right femoral vein (RFV) as shown. Note that while not shown, a snare may be positioned in the IVC as discussed in connection with FIG. 6A (snare 150) for later use in withdrawing an end of the cable out the RSV.

Figure 17:
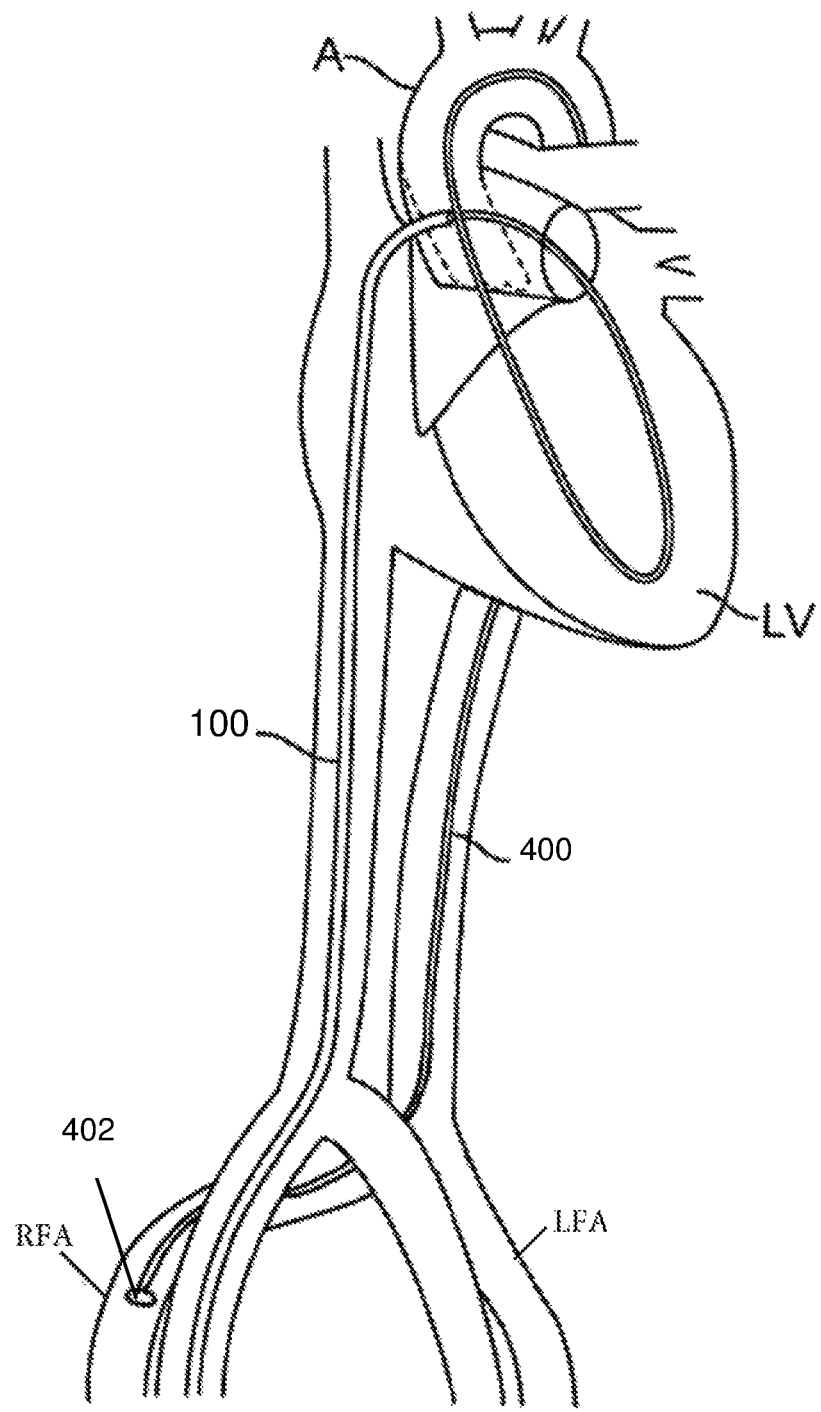
FIG. 17 is a schematic illustration of the heart depicting the tracker balloon being carried by the flow of blood from the left atrium, into and through the aorta, to the femoral artery.
Figure 18:
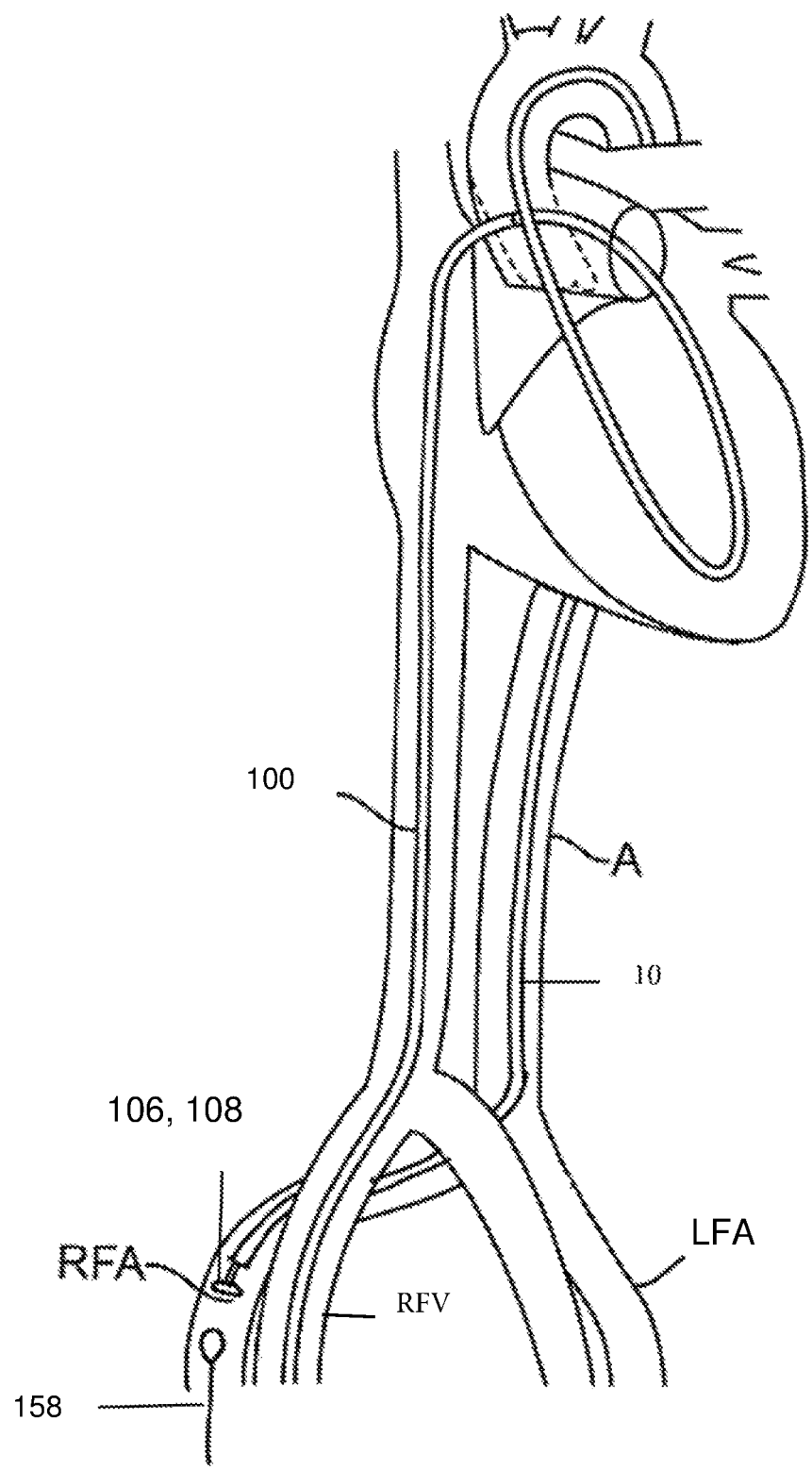
FIG. 18 is similar to FIG. 17, and shows advancement of the RLC over the conveyor cable after the tracker balloon was removed and replaced with the cable. The tip of the cable is then extracted through the femoral artery sheath using a snare.

Once the distal end of the RLC 100 is disposed in the left atrium, the needle is withdrawn and the balloon 402 of the tracker balloon catheter 400 is passed through the RLC into the left atrium. See FIG. 16B. The balloon 402 may have a similar configuration to the balloon described with respect to FIGS. 5A-5C, including an invaginated proximal end to capture the blood flow as it is carried through the circulation as described below. Once deployed within the left atrium, the flow of blood carries the tracker balloon into and through the aorta to the femoral artery as shown in FIG. 17. As discussed previously, this description describes right femoral artery (RFA) access to the arterial vasculature, but in alternative methods the tracker balloon catheter 400 may be diverted to the left femoral artery (LFA). The RLC 100 is then advanced towards the distal end of the tracker balloon catheter 400 towards the femoral artery, and the tracker balloon catheter is then exchanged for a conveyor cable 106 by withdrawing the tracker balloon catheter from the RLC at the femoral vein RFV and replacing it with the cable 106. The end 108 of the cable 106 is advanced through the RLC and out the distal end of the RLC and is captured with a snare 158 (FIG. 18) and withdrawn from the RFA via the right femoral artery sheath (not shown). At this point the cable 106 extends through the RLC 100 between the RFA and the RFV. From here the method proceeds as shown in FIGS. 11-15 and as described above in the corresponding description.

All patents and patent applications referred to herein, including for purposes of priority, are fully incorporated herein by reference.

We claim:

1. A method of delivering a percutaneous ventricular assist device (pVAD) or other cardiac therapeutic device to a target site in the heart, comprising the steps of:
   (a) positioning a flexible member in a body of a patient to run between a femoral artery, through the heart via an aortic valve, left ventricle, mitral valve, left atrium, and right atrium into the venous vasculature, the flexible member having a first end extending outside the body from a venous vessel superior to the heart and a second end external to the patient at the femoral artery, wherein positioning the flexible member includes:
      (i) advancing a right-to-left conveyor (RLC) into the vasculature from a femoral vein, and advancing the RLC to the right atrium and through a transseptal puncture into the left atrium, the RLC having a lumen with a distal opening;
      (ii) advancing the RLC from the left atrium through the mitral valve into the left ventricle;
      (iii) advancing the RLC while rotating to cause the distal opening to orient towards the aortic valve;
      (iv) advancing a wire through the RLC through the aortic valve to the descending aorta;
      (v) advancing the RLC over the wire to the descending aorta;
      (vi) withdrawing the wire from RLC at the femoral vein,
      (vii) introducing a cable into the RLC at the femoral vein and advancing a first end of the cable to the descending aorta;
      (viii) capturing the first end of the cable in the descending aorta and withdrawing it from the femoral artery until a second end of the cable is positioned in a vena cava;
      (ix) engaging the first end of the flexible member to the first end of the cable, after the flexible member had been passed through the LVR outside the femoral artery sheath, and
      (x) capturing the second end of the cable in the vena cava and withdrawing the second end out of the body from a venous vessel;
      (xi) from the venous vessel, snaring the cable out of the vena cava thereby drawing the first end of the flexible member out the venous vessel;

(b) providing a left ventricle redirector (LVR) having a tubular lumen and a distal end, and positioning the LVR over a portion of the flexible member with the LVR's proximal end external to the femoral artery and its distal end within the heart, (c) releasably coupling the first end of the flexible member to a cardiac therapeutic device outside the venous vessel superior to the heart;

(d) pushing the cardiac therapeutic device in a distal direction from the venous vessel while pulling the second end of the flexible member from the femoral artery to advance the cardiac therapeutic device into the heart and into contact with the distal end of LVR within the heart;

(e) advancing the cardiac therapeutic device to a target site in the heart while maintaining it in contact with the LVR, the LVR having sufficient column strength to contain the flexible member and maintain its position away from the cardiac valve structures;

(f) releasing the first end of the flexible member from the cardiac therapeutic device, and withdrawing the flexible member and the LVR from the heart and vasculature, leaving the cardiac therapeutic device at the target site.

2. The method of claim 1, wherein: step (b) includes positioning the LVR over a portion of the flexible member with its distal end within the left ventricle of the heart, and step (d) includes advancing the cardiac therapeutic device such that it makes contact with the distal end of LVR within the left ventricle.

3. The method of claim 2, wherein the distal end of the LVR is actively steerable to form a curve, and wherein:

the method includes:

actively steering the LVR to form the curve;

positioning the curve in an apex of the left ventricle, with a distal opening of the LVR oriented towards the mitral valve, and step (e) includes advancing the cardiac therapeutic device from the left ventricle and into the aortic valve while maintaining it in contact with the LVR.

4. The method of claim 3, wherein the method includes actively locking the LVR to maintain the curve during at least a portion of step (e).

5. The method of claim 1, wherein the target site is an aortic valve site.

6. The method of claim 5 wherein the cardiac therapeutic device is a pVAD.

7. The method of claim 6, wherein the pVAD has an elongate flexible advancer on its distal end, and wherein step (c) includes engaging the advancer and the first end of the flexible member.

8. The method of claim 7, wherein engaging the advancer includes engaging a portion of the advancer using a grasper on the first end of the flexible member.

9. The method of claim 8, wherein engaging the portion of the advancer with a grasper includes grasping the advancer using a moveable jaw member.

10. The method of claim 8, wherein engaging the portion of the advancer with a grasper includes capturing the advancer using a snare.

11. The method of claim 5, wherein the cardiac therapeutic device is a device for treating an aortic valve.

12. The method of claim 11, wherein the device for treating an aortic valve is an aortic valve replacement delivery device.

13. The method of claim 8, wherein engaging the advancer with a grasper includes engaging the advancer with an internal or external collet or suture connection.

\* \* \* \* \*